United States Patent [19]

Baker et al.

[11] Patent Number: 5,097,492

[45] Date of Patent: * Mar. 17, 1992

[54] AUTOMATED LAMINOGRAPHY SYSTEM FOR INSPECTION OF ELECTRONICS

[75] Inventors: Bruce D. Baker, Olivenhain; Robert L. Corey, San Diego; John A. Adams; Edward W. Ross, both of Escondido, all of Calif.

[73] Assignee: Four Pi Systems Corporation, San Diego, Calif.

[ * ] Notice: The portion of the term of this patent subsequent to May 15, 2007 has been disclaimed.

[21] Appl. No.: 479,092

[22] Filed: Feb. 12, 1990

Related U.S. Application Data

[63] Continuation of Ser. No. 115,171, Oct. 30, 1987, Pat. No. 4,926,452.

[51] Int. Cl.$^5$ .............................................. G01N 23/04
[52] U.S. Cl. ........................................ 378/22; 378/25; 378/4; 378/58; 378/62; 378/99; 378/205
[58] Field of Search ...................... 378/12, 14, 22, 10, 378/93, 122, 137, 138, 99, 143, 145, 62, 57, 58, 56, 113, 124, 205, 25

[56] References Cited

U.S. PATENT DOCUMENTS

| | | | |
|---|---|---|---|
| 2,319,350 | 5/1943 | Schiebold | 378/119 |
| 2,511,853 | 6/1950 | Kaiser | 378/146 |
| 2,667,585 | 1/1954 | Gradstein | 378/22 |
| 2,720,596 | 10/1955 | Acker | 378/25 |
| 2,890,349 | 6/1959 | Huszar | 378/145 |
| 2,998,518 | 8/1961 | Guntert | 378/22 |
| 3,091,692 | 5/1963 | Verse | 378/22 |

FOREIGN PATENT DOCUMENTS

| | | | |
|---|---|---|---|
| 1138617 | 10/1962 | Fed. Rep. of Germany | 378/25 |
| 0143290 | 11/1979 | Japan . | |

OTHER PUBLICATIONS

LeClair, "Nondestructive Measurement and Inspection Process", IBM Technical Disclosure Bulletin, vol. 18, No. 12, May 1976.

Phelps, Christi, "Four Pi Captures Contract, Capital; Unveils Product", San Diego Business Journal, Week of Oct. 10-16, 1988.

Hasenkamp, "Radiographic Laminography", Materials Evaluation, Aug. 1974, pp. 169-180.

Moler, "Development of a Continuous Scanning Laminograph", Final Report No. IITRI V6034-24, Oct. 1968.

(List continued on next page.)

Primary Examiner—Edward P. Westin
Assistant Examiner—Don Wong
Attorney, Agent, or Firm—Knobbe, Martens, Olson & Bear

[57] ABSTRACT

A tomographic inspection system wherein the electron beam of a microfocus X-ray tube is deflected in a circular scan pattern onto the tube anode in synchronization with a rotating detector that converts the X-ray shadowgraph into an optical image and derotates the image so as to be viewed and integrated in a stationary video camera. A computer system controls an automated positioning system that supports the item under inspection and moves successive areas of interest into view. In order to maintain high image quality, a computer system also controls the synchronization of the electron beam deflection and rotating optical system, making adjustments for inaccuracies of the mechanics of the system. The computer system can also operate under program control to automatically analyze data, measure characteristics of the item under inspection and make decisions regarding the acceptability of the item's quality. The invention produces high resolution images in rapid succession so as to be suitable for use in conjunction with manufacturing production lines and capable of inspecting electronic devices, solder connections, printed wiring boards and other assemblies.

44 Claims, 20 Drawing Sheets

U.S. PATENT DOCUMENTS

Blanche, "Nondestructive Testing Techniques for Multilayer Printed Wiring Boards", Nondestructive Testing: Trends and Techniques, NASA SP-5082, 10/86, pp. 1-13.
Hamre, "Nondestructive Testing Techniques for Multilayer Printed Wiring Boards", Report No. IITRI-E60-24-15, Sep. 1965.
Kruger et al., "Industrial Applications of Computed Tomography at Los Alamos Scienific Laboratory", LA-8412-MS, Jun. 1980.
Stanley et al., "A New NDE Capability for Thin-Shelled Structures", AFWAL-TR-84-4120, Materials Lab, Wright Patterson AFB, Sep. 1984.
Deane et al., IRT Corp., "Using X-Ray Vision to Verify SMD-Board Quality", *Electronics Test,* Feb. 1987, pp. 32-35.
Soron, IRT Corp., "X-Ray Inspection Meets Increased PWB Throughput, Density Challenge—Part 1", *Electronics,* Oct. 1987, pp. 36-37.
Pound, "Image Processing Boosts the Power of Non-Destructive Testing", *Electronic Packaging and Production,* Jun. 1985.
Casey, "X-Ray Inspection", *Manufacturing Systems,* Jul. 1987, pp. 18ff.
Corey, IRT Corp., "Artificial Perception Gives Super Vision", *Research and Development,* Oct. 1984.
Hufault et al., "Lead-Indium Solder Joint Analysis", IBM Technical Disclosure Bulletin, vol. 19, No. 11, Apr. 1977.
Wittenberg, "IRT Improves SMT X-Ray Inspection System", *Electronic Engineering Times,* Oct. 5, 1987, p. 53.

OTHER PUBLICATIONS

| Patent No. | Date | Inventor | Class |
|---|---|---|---|
| 3,149,257 | 9/1964 | Wintermute | 378/137 |
| 3,742,229 | 6/1973 | Smith et al. | 378/34 |
| 3,780,291 | 12/1973 | Stein et al. | 378/146 |
| 3,832,546 | 8/1974 | Morsell et al. | 250/315 |
| 3,843,225 | 10/1974 | Kock et al. | 350/3.5 |
| 3,894,234 | 7/1975 | Mauch et al. | 378/146 |
| 3,928,769 | 12/1975 | Smith | 378/22 |
| 3,962,579 | 6/1976 | Winnek | 378/145 |
| 3,984,684 | 10/1976 | Winnek | 378/145 |
| 4,002,917 | 1/1977 | Mayo | 378/14 |
| 4,007,375 | 2/1977 | Albert | 378/137 |
| 4,032,785 | 6/1977 | Green et al. | 378/61 |
| 4,075,489 | 2/1978 | Neal et al. | 378/137 |
| 4,107,563 | 8/1978 | Oddell | 378/126 |
| 4,130,759 | 12/1978 | Haimson | 378/10 |
| 4,139,776 | 2/1979 | Hellstrom | 378/22 |
| 4,211,927 | 7/1980 | Hellstrom et al. | 250/445 T |
| 4,228,353 | 10/1980 | Johnson | 378/6 |
| 4,234,792 | 11/1980 | DeCou et al. | 378/19 |
| 4,260,898 | 4/1981 | Annis | 378/146 |
| 4,287,425 | 9/1981 | Elliott, Jr. | 378/137 |
| 4,340,816 | 7/1982 | Schott | 250/403 |
| 4,352,021 | 9/1982 | Boyd et al. | 378/12 |
| 4,385,434 | 5/1983 | Zehnpfennig et al. | 378/34 |
| 4,400,620 | 8/1983 | Blum | 250/363.05 |
| 4,414,682 | 11/1983 | Annis et al. | 378/146 |
| 4,415,980 | 11/1983 | Buchanan | 378/58 |
| 4,426,722 | 1/1984 | Fujimura | 378/137 |
| 4,472,824 | 9/1984 | Buckley | 378/205 |
| 4,481,664 | 11/1984 | Linger et al. | 356/394 |
| 4,491,956 | 1/1985 | Winnek | 378/41 |
| 4,516,252 | 5/1985 | Linde et al. | 378/2 |
| 4,628,531 | 12/1986 | Okamoto et al. | 382/34 |
| 4,688,939 | 8/1987 | Ray | 250/572 |
| 4,731,855 | 3/1988 | Suda et al. | 382/8 |
| 4,803,639 | 2/1989 | Steele et al. | 378/58 |
| 4,809,308 | 2/1989 | Adams et al. | 378/58 |
| 4,852,131 | 7/1988 | Armistead | 378/58 |
| 4,926,452 | 5/1990 | Baker et al. | 378/22 |

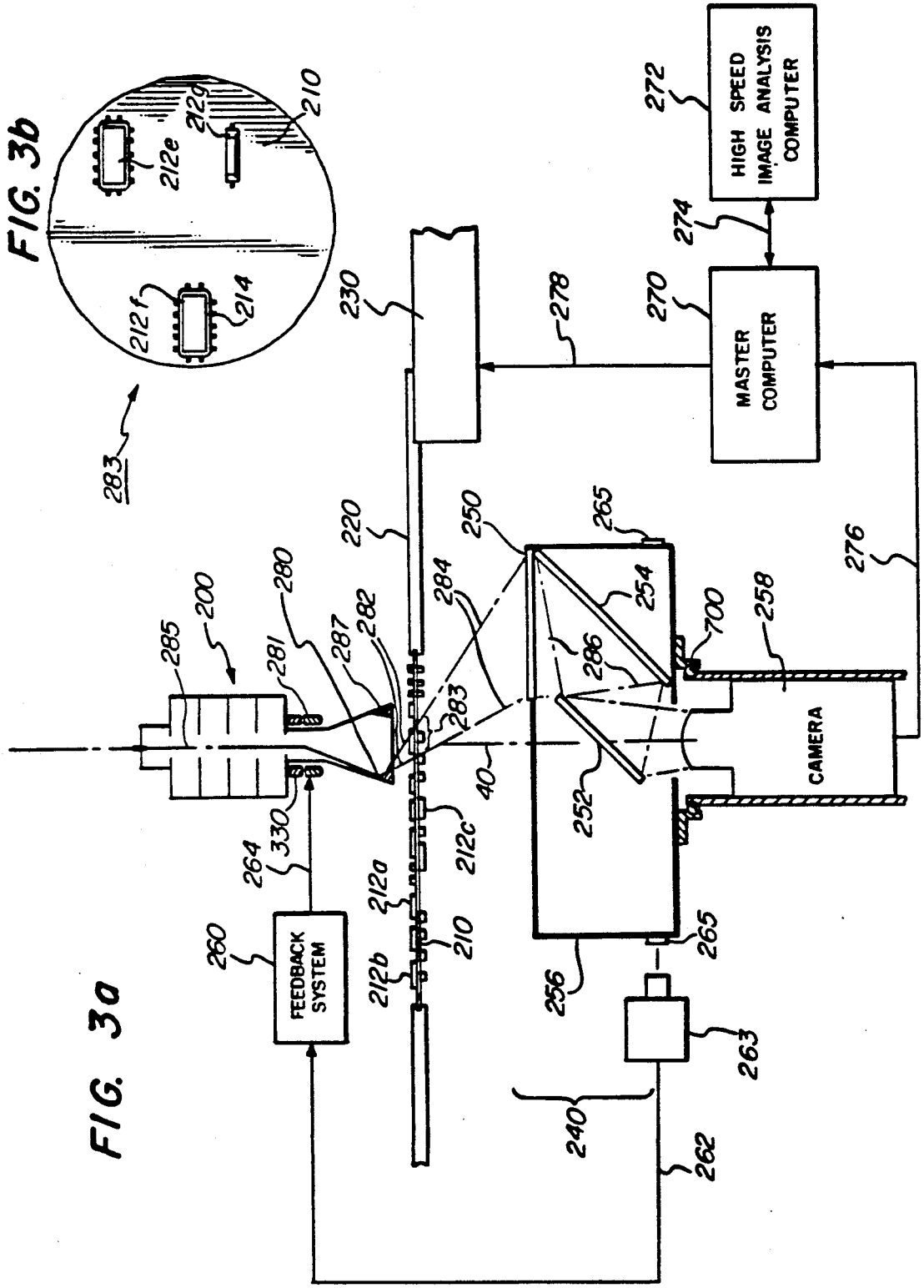

AUTOMATED LAMINOGRAPHY SYSTEM FOR INSPECTION OF ELECTRONICS

This application is a continuation of application Ser. No. 115,171, filed Oct. 10, 1987 now U.S. Pat. No. 4,926,452.

FIELD OF THE INVENTION

The invention relates generally to the art of tomography, especially to a computerized laminography system for rapid, high resolution inspection of manufactured electronic items.

BACKGROUND OF THE INVENTION

Rapid and precise quality control inspections of the soldering and assembly of electronic devices have become priority items in the electronics manufacturing industry. The reduced size of components and solder connections, the resulting increased density of components on circuit boards and the advent of surface mount technology (SMT), which places solder connections underneath device packages where they are hidden from view, have made rapid and precise inspections of electronic devices and the electrical connections between devices very difficult to perform in a manufacturing environment.

Many existing inspection systems for electronic devices and connections make use of penetrating radiation to form images which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is detected and recorded by an X-ray sensitive material such as film or other suitable means.

The appearance of the X-ray shadow or radiograph is determined not only by the internal structural characteristics of the object, but also by the direction from which the incident X-rays strike the object. Therefore, a complete interpretation and analysis of X-ray shadow images, whether performed visually by a person or numerically by a computer, often requires that certain assumptions be made regarding the characteristics of the object and its orientation with respect to the X-ray beam. For example, it is often necessary to make specific assumptions regarding the shape, internal structure, etc. of the object and the direction of the incident X-rays upon the object. Based on these assumptions, features of the X-ray image may be analyzed to determine the location, size, shape, etc., of the corresponding structural characteristic of the object, e.g., a defect in a solder connection, which produced the image feature. These assumptions often create ambiguities which degrade the reliability of the interpretation of the images and the decisions based upon the analysis of the X-ray shadow images. One of the primary ambiguities resulting from the use of such assumptions in the analysis of conventional radiographs is that small variations of a structural characteristic within an object, such as the shape, density and size of a defect within a solder connection, are often masked by the overshadowing mass of the solder connection itself as well as by neighboring solder connections, electronic devices, circuit boards and other objects. Since the overshadowing mass and neighboring objects are usually different for each solder joint, it is extremely cumbersome and often nearly impossible to make enough assumptions to precisely determine shapes, sizes and locations of solder defects within individual solder joints.

In an attempt to compensate for these shortcomings, some systems incorporate the capability of viewing the object from a plurality of angles. The additional views enable these systems to partially resolve the ambiguities present in the X-ray shadow projection images. However, utilization of multiple viewing angles necessitates a complicated mechanical handling system, often requiring as many as five independent, non-orthogonal axes of motion. This degree of mechanical complication leads to increased expense, increased size and weight, longer inspection times, reduced throughput, impaired positioning precision due to the mechanical complications, and calibration and computer control complications due to the non-orthogonality of the axes of motion.

Many of the problems associated with the conventional radiography techniques discussed above may be alleviated by producing cross-sectional images of the object being inspected. Tomographic techniques such as laminography and computed tomography (CT) are often used in medical applications to produce cross-sectional or body section images. In medical applications, these techniques have met with widespread success, largely because relatively low resolution on the order of one or two millimeters (0.04 to 0.08 inches) is satisfactory and because speed and throughput requirements are not as severe as the corresponding industrial requirements. However, no laminography inspection system has yet met with commercial success in an industrial application because of shortcomings in precision and/or speed of inspection. This is because existing laminography systems have been incapable of achieving the high positional accuracies and image resolutions necessary to solve industrial inspection problems while operating at the speeds necessary to make them practical in a production environment.

In the case of electronics inspection, and more particularly, for inspection of electrical connections such as solder joints, image resolution on the order of several micrometers, for example, 20 micrometers (0.0008 inches) is necessary. Furthermore, an industrial solder joint inspection system must generate multiple images per second in order to be practical for use on an industrial production line. Heretofore, laminography systems have not been able to achieve these speed and accuracy requirements necessary for electronics inspection.

Laminography systems for the production of cross-sectional images have taken several forms. One system is described in U.S. Pat. No. 3,928,769 entitled "LAMINOGRAPHIC INSTRUMENT." The radiation source and the detector described therein are mechanically coupled to achieve the required geometry and synchronized motion of the source and detector. This type of system has the disadvantage of having to move the relatively high mass of some combination of high mass elements including the radiation source, object under inspection and detector. This becomes especially difficult when X-ray tubes and camera equipment are to be used. The speed of this system is severely restricted due to the fact that it is extremely difficult to move these relatively large masses rapidly and precisely. This system also has limitations on the resolution that can be obtained due to the imprecision and degradation over time of the many complicated moving parts.

In another system described in U.S. Pat. No. 4,211,927 entitled "COMPUTERIZED TOMOGRAPHY SYSTEM," the mechanical motions of the radiation source and detector are electronically driven by separate stepper motors whose timing is controlled by the same computer. The motion of each component is referenced to a respective predetermined central calibration location. Thus, even though the source and detector are driven by the same computer, there is no direct link correlating the position of the source with the position of the detector. The performance of this system is also limited by the speed at which the massive radiation source and detector can be oscillated and by the precision, synchronization and stability of the moving parts.

In U.S. Pat. No. 4,516,252 entitled "DEVICE FOR IMAGING LAYERS OF A BODY," a plurality of radiation sources, each fixed in space at a different location, is used in lieu of a single oscillating source. The location of an image detector is moved electronically in synchronization with the activation of the plural sources. While this approach eliminates the problems inherent with mechanically moving the radiation source and detector, it entails the disadvantage in cost of requiring multiple radiation sources. The resulting image quality is also degraded because the desired blurring of out of focus features is not continuous, but rather discretized, due to the finite number of radiation source positions. Thus, unwanted features remain in the image as a plurality of distinct artifacts.

U.S Pat. No. 2,667,585 entitled "DEVICE FOR PRODUCING SCREENING IMAGES OF BODY SECTIONS" shows a stationary X-ray tube with the radiation source motion provided by electrostatic deflection of the electron beam in the X-ray tube, thus causing the electron beam to trace a path over the surface area of a flat target anode. Opposite the X-ray tube is a detector image tube containing electron optics which deflect the resulting electron image onto a stationary detector. The deflection circuit of the X-ray tube and the deflection circuit of the image tube are driven from the same voltage supply so as to simultaneously drive the motion of the X-ray source and the deflection of the resultant image in the detector. This system thus avoids many of the disadvantages associated with mechanically moving the radiation source and detector. However, this system has no provision for consistently maintaining the focus and energy of the electron beam as the beam is swept over the target surface. This causes the X-ray spot to vary in both size and intensity, which seriously limits the resolution achievable with the device. The use of electron optics to deflect the electron image also limits the detection resolution achievable with this device. This problem becomes especially severe as the image is deflected through large angles. Similarly, accuracy in the positioning of the X-ray spot is lost as the beam is deflected through severe angles. These characteristics substantially limit the resolution achievable with this technique. Furthermore, the technique is practical only for operation within a relatively small range of viewing angles, which limits the desired laminographic blurring effect of unwanted features and consequently limits the resolution in a direction normal to the plane of focus.

All of the above described laminography systems are directed to performing body section radiography and, as such, are not designed to produce high resolution images in rapid succession. Furthermore, such systems need not operate in a continuous duty cycle nor in an environment compatible with the manufacturing of electronics.

Many of the deficiencies found in presently used electronic inspection systems could be overcome with a high resolution, high speed laminographic inspection system. Such a system would be particularly well suited for the inspection of electrical connections such as solder joints in electronic assemblies. A high resolution laminograph of a solder joint should be capable of unambiguously revealing features in the solder joint which are indicative of the joint quality. Unfortunately, even though many attempts have been made to utilize laminographic techniques in industrial inspection environments, prior systems have consistently fallen short of optimum performance because of poor image resolution or prohibitively long inspection times, or both. Techniques previously used to improve resolution invariably resulted in long inspection times. Likewise, techniques previously used to decrease inspection time have generally sacrificed image resolution. A need thus exists for a high speed, high resolution industrial laminography system capable of inspecting electronics in industrial environments.

SUMMARY OF THE INVENTION

The present invention is directed to an apparatus and method for the inspection of electrical connections between electronic components which are mounted on printed circuit boards. The invention produces cross-sectional images of the connections which are then analyzed by a computer aided image analysis system. The cross-sectional images are automatically analyzed to identify and locate defects in the connections and to determine process characteristics of the connections. A report of the image analysis indicating the location and type of defect or process characteristic is prepared and presented to the user.

More specifically, the present invention provides an automated laminography inspection system for solder joints on printed wiring board assemblies and other electronic devices and assemblies. A central data processing and control unit positions the item to be inspected, controls the formation of the laminographic images, analyzes the image data, makes decisions regarding the characteristics and acceptability of the item being inspected based on analysis of the image data and communicates the results of the inspection process to the user.

The inspection system of the present invention has several significant advantages over alternative systems and methods. Thus, the present invention's performance is superior to these alternate systems and methods due in part to the high resolution of the images, the cross-sectional format of the images, and the automated rapid acquisition and analysis of the images.

The invention advantageously utilizes the techniques of X-ray laminography to acquire the high resolution cross-sectional images. The invention employs circular motions of a radiation source and detector in order to optimize the laminographic blurring of artifacts without resorting to unnecessarily complex motions. Precision circular rotation of the radiation source is effected by causing the electron beam within a stationary X-ray tube to circumscribe a circular path on the anode of the X-ray tube, thus eliminating moving parts associated with rotation of the radiation source. Rotation of the detector is the only mechanical motion required to generate the laminographic image. A calibrated feedback system further improves the precision of the system by compensating for inaccuracies in the mechanical components of the system which affect the alignment and synchronization of the rotating X-ray source and detector during formation of the laminographic images. The feedback system coordinates the detector location with the X-ray source location thus ensuring the continuous and accurate alignment of the source and detector during acquisition of the images.

The high resolution, high speed laminography inspection system of the present invention produces high resolution cross-sectional images of solder connections, electronic devices and other assemblies while maintaining high inspection rates in the following manner. The rotating X-ray source and detector produce a rotating X-ray shadowgraph image which impinges upon a fluorescent screen detector that converts the X-ray image into a visible light image. Rotation of the X-ray source is accomplished electronically, thus eliminating inaccurate and complicated mechanical mechanisms. The fluorescent screen is carried on a turntable positioned opposite the rotating X-ray source. The screen rotates in a plane which is parallel to the plane defined by the locus of the rotating X-ray source and rotates about a common axis of rotation with the X-ray source. Also mounted on the turntable is an optical derotation assembly comprising two mirrors which allows the image on the fluorescent screen to be viewed by a stationary camera. Thus the only mechanical motion required to form a cross-sectional image is the rotation of the turntable, which can be rotated at a constant speed, making the mechanical aspects of the system quite simple.

Image resolution is further improved by using a microfocus X-ray source in an arrangement which provides geometric magnification of the object being inspected.

Precise alignment of the source and detector also contributes to the production of high resolution images and is maintained by a feedback system. The feedback system maintains precise alignment of the rotating source spot and fluorescent screen by driving the deflection circuitry of the electron beam within the X-ray tube in synchronization with the position of the rotating turntable. This feedback technique allows for greater accuracy than in prior laminography systems by storing in a memory a look-up table of coordinates that indicate the precise signals to be issued to the deflection circuitry of the X-ray source based upon the actual position of the turntable as determined by a precision position encoder. The feedback system accepts from the position encoder input data indicating the position of the turntable, retrieves the corresponding coordinates from the look-up table and drives the deflection circuitry on the X-ray tube accordingly. The alignment of the source spot and turntable is periodically calibrated in a procedure that generates an appropriate look-up table of coordinates. Thus the precision of the laminography system is maintained in spite of minor inaccuracies and variations in the speed of rotation of the turntable, the alignment of the turntable, the shape of the target anode and other critical parameters determining the inspection geometry.

The printed wiring board, or other object to be inspected, is supported on a mechanical handling system that can be operated automatically under computer control to move the object in a fashion that sequentially brings the desired portions of the object into view.

The high resolution cross-sectional image of a solder joint acquired by the X-ray laminography system is analyzed automatically. A powerful computer system utilizes parallel processing to efficiently and automatically control the acquisition of a cross-sectional image of the solder joint, measure characteristics of the image, correlate the characteristics with specific types of solder defects and make decisions regarding the acceptability of the item's quality accordingly. The results of the image analysis are communicated to the user in any of a variety of output formats.

These and other characteristics of the present invention will become apparent through reference to the accompanying drawings.

BRIEF DESCRIPTION OF THE DRAWINGS

FIG. 2e shows a conventional, two-dimensional X-ray projection image of the object in FIG. 2a.

FIG. 3a is a diagrammatic cross-sectional view of a first preferred embodiment of the image forming apparatus of the invention, showing how the laminographic image is formed and viewed by a camera.

FIG. 3b shows a top view enlargement of an inspection region shown in FIG. 3a.

FIG. 3c is a perspective view of the embodiment of the invention shown in FIG. 3a.

FIG. 9b shows an X-ray image of the test fixture of FIG. 9a.

FIG. 10b is a continuation of the flowchart in FIG. 10a.

FIG. 20b is a continuation of the flowchart in FIG. 20a.

DETAILED DESCRIPTION OF THE PREFERRED EMBODIMENT

As used throughout, the term "radiation" refers to electromagnetic radiation, including but not limited to the X-ray, gamma and ultraviolet portions of the electromagnetic radiation spectrum.

Figure 1:
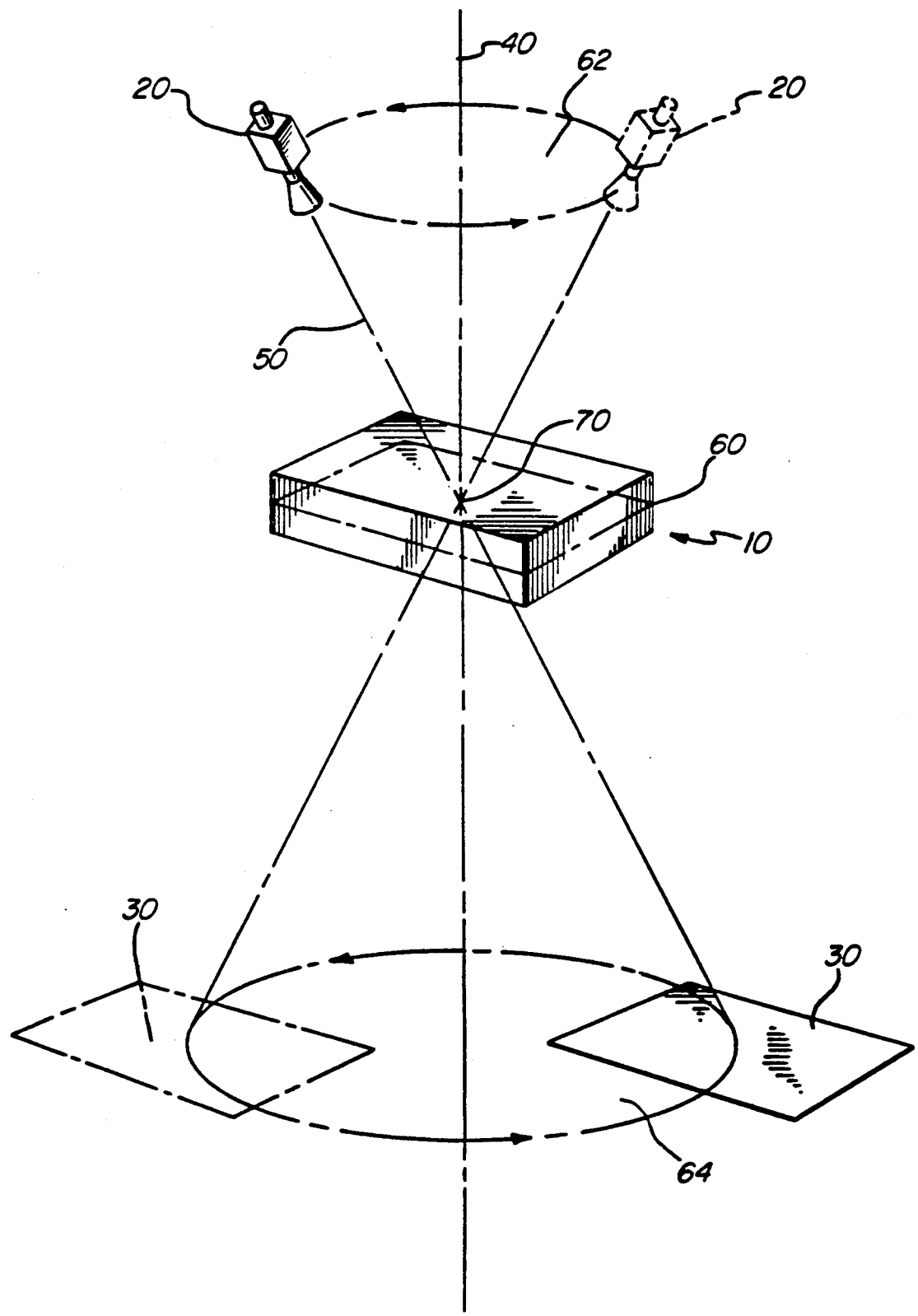
FIG. 1 is a schematic representation of a laminography system illustrating the principles of the technique.

FIG. 1 shows a schematic representation of the laminographic geometry used in the present invention. An object 10 under examination, for example, a circuit board, is held in a stationary position with respect to a source of X-rays 20 and an X-ray detector 30. Synchronous rotation of the X-ray source 20 and detector 30 about a common axis 40 causes an X-ray image of the plane 60 within the object 10 to be formed on the detector 30. The image plane 60 is substantially parallel to the planes 62 and 64 defined by the rotation of the source 20 and detector 30, respectively. The image plane 60 is located at the intersection 70 of a central ray 50 from the X-ray source 20 and the common axis of rotation 40. This point of intersection 70 acts as a fulcrum for the central ray 50, thus causing an in-focus cross-sectional X-ray image of the object 10 at the plane 60 to be formed on detector 30 as the source and detector synchronously rotate about the intersection point 70. Structure within the object 10 which lies outside of plane 60 forms a blurred X-ray image on detector 30.

The laminographic geometry shown in FIG. 1 is the geometry preferred for the present invention. However, it is not necessary that the axis of rotation of the radiation source 20 and the axis of rotation of the detector 30 be coaxial. The conditions of laminography are satisfied and a cross-sectional image of the layer 60 will be produced as long as the planes of rotation 62 and 64 are mutually parallel, and the axes of rotation of the source and the detector are mutually parallel and fixed in relationship to each other. This reduces the number of contraints upon the mechanical alignment of the apparatus of the present invention.

FIGS. 2a-2e show laminographs produced by the above described laminographic technique. The object 10 shown in FIG. 2a has test patterns in the shape of an arrow 81, a circle 82 and cross 83 embedded within the object 10 in three different planes 60a, 60b and 60c, respectively.

Figure 2A:
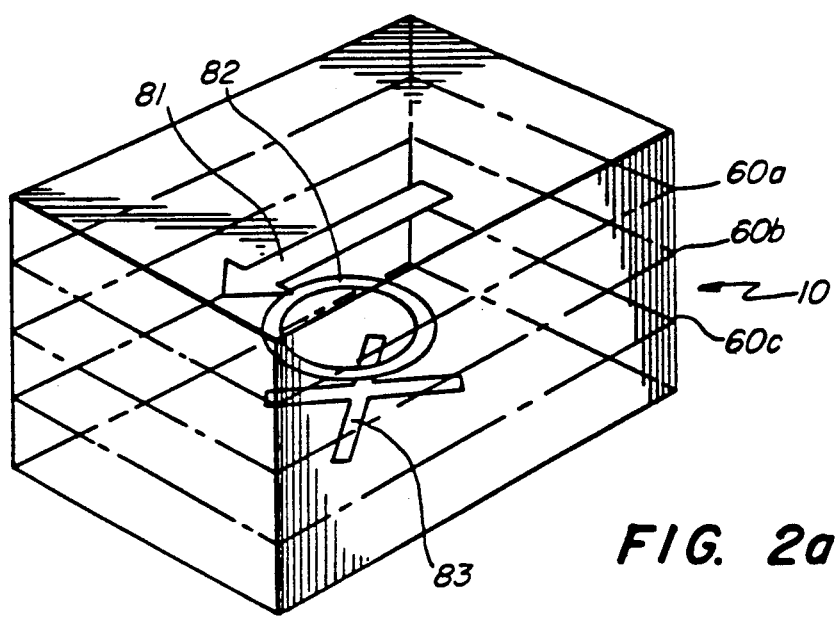
FIG. 2a shows an object having an arrow, a circle and a cross embedded in the object at three different planar locations.
Figure 2B:
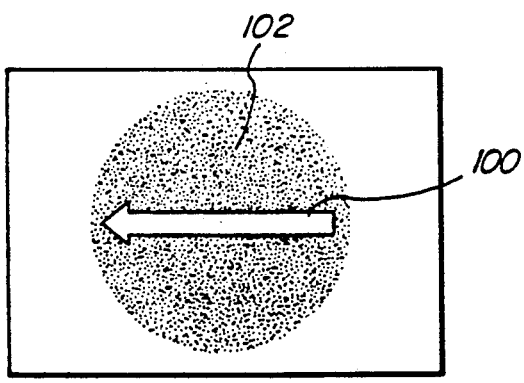
FIG. 2b shows a laminograph of the object in FIG. 2a focused on the plane containing the arrow.

FIG. 2b shows a typical laminograph of object 10 formed on detector 30 when the point of intersection 70 lies in plane 60a of FIG. 2a. The image 100 of arrow 81 is in sharp focus, while the images of other features within the object 10, such as the circle 82 and cross 83 form a blurred region 102 which does not greatly obscure the arrow image 100.

Figure 2D:
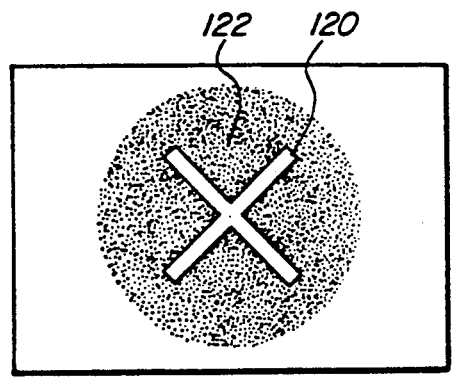
FIG. 2d shows a laminograph of the object in FIG. 2a focused on the plane containing the cross.
Figure 2C:
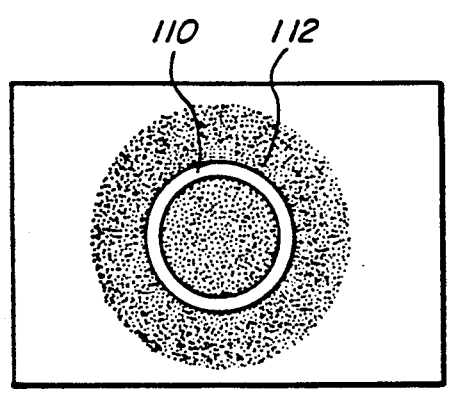
FIG. 2c shows a laminograph of the object in FIG. 2a focused on the plane containing the circle.

Similarly, when the point of intersection 70 lies in plane 60b, the image 110 of the circle 82 is in sharp focus as seen in FIG. 2c. The arrow 81 and cross 83 form a blurred region 112.

FIG. 2d shows a sharp image 120 formed of the cross 83 when the point of intersection 70 lies in plane 60c. The arrow 81 and circle 82 form blurred region 122.

Figure 2E:
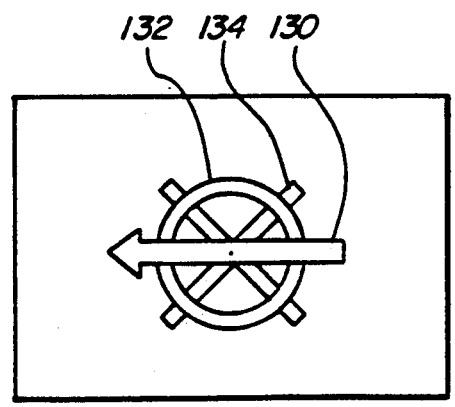

For comparison, FIG. 2e shows an X-ray shadow image of object 10 formed by conventional projection radiography techniques. This technique produces sharp images 130, 132 and 134 of the arrow 81, circle 82 and cross 83, respectively, which overlap one another. FIG. 2e vividly illustrates how multiple characteristics contained within the object 10 may create multiple overshadowing features in the X-ray image which obscure individual features of the image.

FIG. 3a illustrates a schematic diagram of a preferred embodiment of the invention. In this preferred embodiment, an object under inspection is a printed circuit board 210 having multiple electronic components 212 mounted on the board 210 and electrically interconnected via electrical connections 214 (see FIG. 3b). Typically, the electrical connections 214 are formed of solder. However, various other techniques for making the electrical connections 214 are well know in the art and even though the invention will be described in terms of solder joints, it will be understood that other types of electrical connections 214 including, but not limited to, conductive epoxy, mechanical, tungsten and eutectic bonds may be inspected utilizing the invention. FIG. 3b, which is a top view enlargement of a region 283 of the circuit board 210, more clearly shows the components 212 and solder joints 214.

The invention acquires cross-sectional images of the solder joints 214 using the previously described laminographic method or other methods capable of producing equivalent cross-sectional images, such as standard computerized tomography techniques. The cross-sectional images of the solder joints 214 are automatically evaluated to determine their quality. Based on the evaluation, a report of the solder joint quality is presented to the user.

The invention, as shown in FIG. 3a, comprises an X-ray tube 200 which is positioned adjacent printed circuit board 210. The circuit board 210 is supported by a fixture 220. The fixture 220 is attached to a positioning table 230 which is capable of moving the fixture 220 and board 210 along three mutually perpendicular axes, X, Y and Z. A rotating X-ray detector 240 comprising a fluorescent screen 250, a first mirror 252, a second mirror 254 and a turntable 256 is positioned adjacent the circuit board 210 on the side opposite the X-ray tube 200. A camera 258 is positioned opposite mirror 252 for viewing images reflected into the mirrors 252, 254 from fluorescent screen 250. A feedback system 260 has an input connection 262 from a sensor 263 which detects the angular position of the turntable 256 and an output connection 264 to X and Y deflection coils 281 on X-ray tube 200. A position encoder 265 is attached to turntable 256. The position sensor 263 is mounted adjacent encoder 265 in a fixed position relative to the axis of rotation 40. The camera 258 is connected to a master computer 270 via an input line 276. The master computer 270 is connected to a high speed image analysis computer 272. Data is transferred between the master computer 270 and the image analysis computer 272 via data bus 274. An output line 278 from master computer 270 connects the master computer to positioning table 230.

Figure 3C:
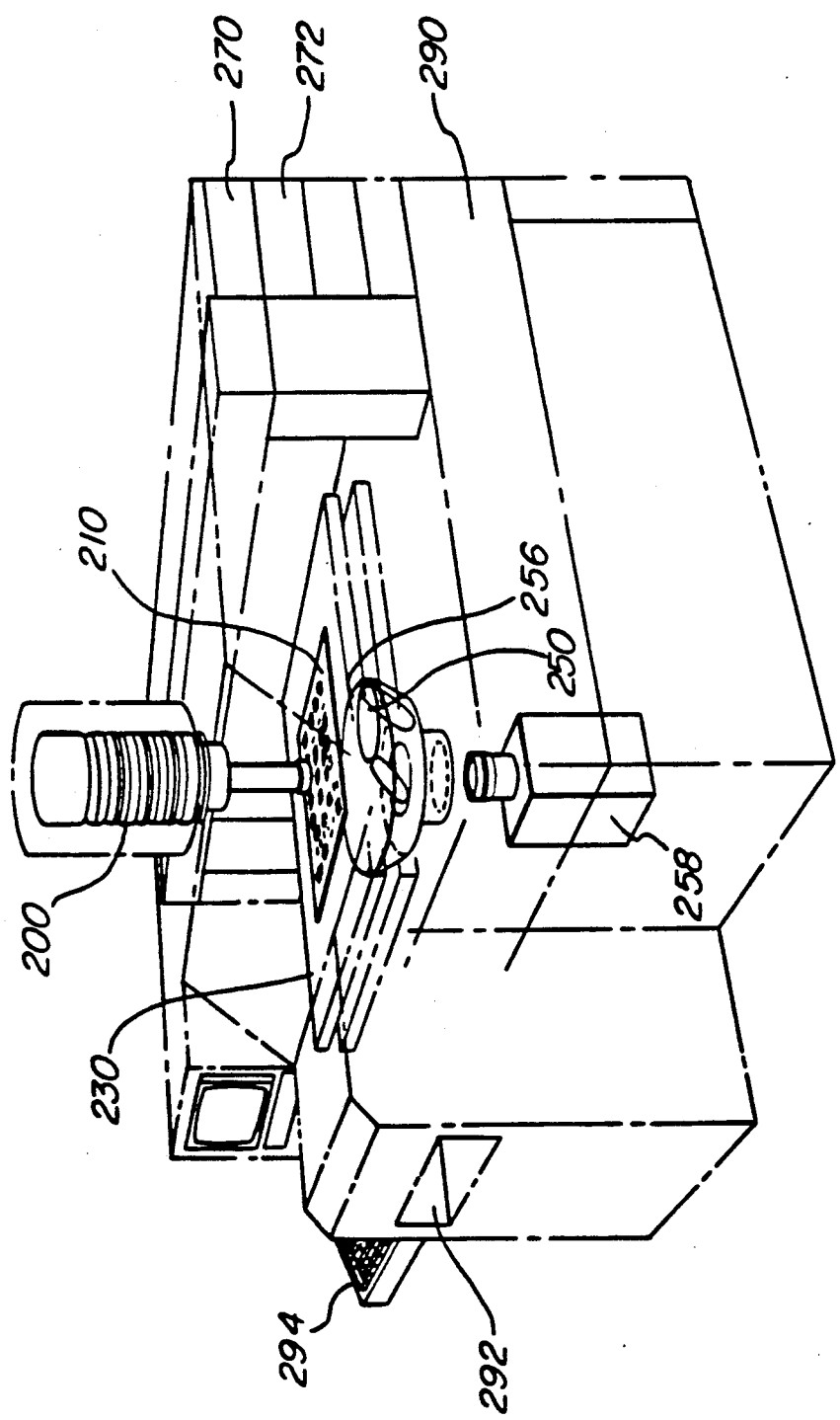

A perspective view of the invention is shown in FIG. 3c. In addition to the X-ray tube 200, circuit board 210, fluorescent screen 250, turntable 256, camera 258, positioning table 230 and computers 270, 272 shown in FIG. 3a, a granite support table 290, a load/unload port 292 and an operator station 294 are shown. The granite table 290 provides a rigid, vibration free platform for structurally integrating the major functional elements of the invention, including but not limited to the X-ray tube 200, positioning table 230 and turntable 256. The load/unload port 292 provides a means for inserting and removing circuit boards 210 from the machine. The operator station 294 provides an input/output capability for controlling the functions of the invention as well as for communication of inspection data to an operator.

In operation of the invention as shown in FIGS. 3a and 3c, high resolution, cross-sectional X-ray images of the solder joints 214 connecting components 212 on circuit board 210 are acquired using the X-ray laminographic method previously described in reference to FIGS. 1 and 2. Specifically, X-ray tube 200, as shown in FIG. 3a, comprises a rotating electron beam spot 285 which produces a rotating source 280 of X-rays 282. The X-ray beam 282 illuminates a region 283 of circuit board 210 including the solder joints 214 located within region 283. X-rays 284 which penetrate the solder joints 214, components 212 and board 210 are intercepted by the rotating fluorescent screen 250.

Dynamic alignment of the position of the X-ray source 280 with the position of rotating X-ray detector 240 is precisely controlled by feedback system 260. The feedback system correlates the position of the rotating turntable 256 with calibrated X and Y deflection values stored in a look-up table (LUT). Drive signals proportional to the calibrated X and Y deflection values are transmitted to the steering coils 281 on the X-ray tube 200. In response to these drive signals, steering coils 281 deflect electron beam 285 to locations on an annular shaped target anode 287 such that the position of the X-ray source spot 280 rotates in synchronization with the rotation of detector 240 in the manner previously discussed in connection with FIG. 1.

X-rays 284 which penetrate the board 210 and strike fluorescent screen 250 are converted to visible light 286, thus creating a visible image of a single plane within the region 283 of the circuit board 210. The visible light 286 is reflected by mirrors 252 and 254 into camera 258. Camera 258 typically comprises a low light level closed circuit TV (CCTV) camera which transmits electronic video signals corresponding to the X-ray and visible images to the master computer 270 via line 276. The electronic video format image is transferred to the high speed image analysis computer 272 via line 274. The image analysis computer 272 analyzes and interprets the image to determine the quality of the solder joints 214.

Master computer 270 also controls the movement of positioning table 230 and thus circuit board 210 so that different regions of circuit board 210 may be automatically positioned within inspection region 283.

ROTATING X-RAY SOURCE

Figure 4:
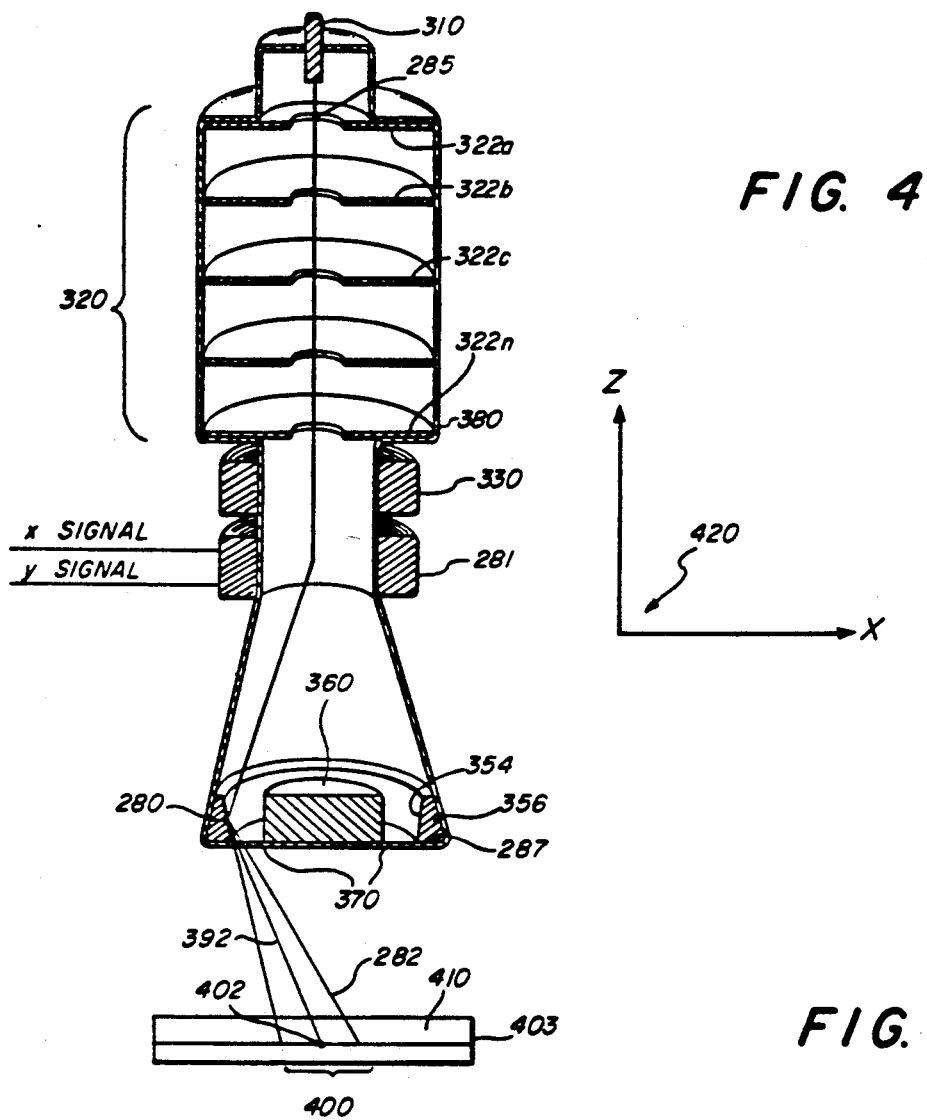
FIG. 4 shows details of an X-ray tube having a rotating spot source of X-rays for use in the preferred embodiment.

FIG. 4 illustrates an X-ray tube 200 capable of providing the rotating beam of X-rays 282 for producing high resolution laminographs of circuit boards. The tube 200 comprises an electron gun 310 mounted adjacent a high voltage electrode section 320. Focus coils 330 and steering coils 281 are positioned intermediate the electrode section 320 and the annular shaped target anode 287. An electron beam stop 360 and X-ray window 370 are mounted within the central area defined by the annular shaped anode 287. A vacuum envelope 380 encloses the evacuated portions of the X-ray tube assembly 200.

In operation, electron gun 310 emits an electron beam 285 into the high voltage electrode section 320. A high DC voltage is applied between the electron gun 310 and target anode 287 to accelerate and guide electron beam 285 toward a collision with the anode 287. Portions of the high voltage signal are applied to electrodes 322 which guide, accelerate, and shape electron beam 285. In a preferred embodiment, the high voltage signal is approximately 160 kilovolts and is capable of providing approximately 7.5 microamps of current through electron beam 285 to anode 287. Preferably, the high voltage signal is maintained constant to within an accuracy of approximately 0.01%. It will be understood that these values are exemplary and that other voltages, currents, and accuracies may also be used.

After traversing electrode section 320, the electron beam 285 enters a region of the tube wherein the shape and direction of the electron beam are affected by the focus coils 330 and steering coils 281. In a preferred embodiment, the coils 330 and 281 produce electromagnetic fields which interact with the electron beam 285 to focus as well as direct the electron beam 285 toward specific locations on the anode 287. The X-ray source 280 coincides with these specific locations from which the X-ray beam 282 is emitted. In this manner, an extremely small, approximately 20-micron diameter electron beam spot is formed on the anode 287 at these locations. As is well known in the field of radiography, the size of this spot plays a very important role in determining the overall resolution of the X-ray images obtained from the source of X-rays 280.

The steering coils 281, in combination with the annular shaped anode 287 enable the X-ray tube 200 to provide X-rays from source 280 wherein the location of the source 280 moves in a circular pattern around the anode. The circular pattern is centered about a fulcrum point 402 located within a cross-sectional image plane 403 of object 410.

Specifically, the steering coils 281 are capable of directing the electron beam 285 toward any desired portion of an inner surface 354 of anode 287. By driving the electromagnetic coils 281 with appropriately synchronized X and Y drive signals, the electron beam 285 can be steered toward the anode 287 such that the beam inscribes a circular path along the inner surface 354 of the anode 287.

In a preferred embodiment, the steering coils 281 comprise separate X and Y electromagnetic coils which deflect electron beam 285 in the X and Y directions respectively. Electrical current flowing in the coils 281 creates magnetic fields which interact with the electron beam 285 causing the beam to be deflected. These coils 281 are similar in structure and function to the yoke coils found in cathode ray tubes (CRT). It will be understood, however, that electrostatic deflection techniques could also be used to deflect the electron beam 285.

The surface 354 upon which the electron beam 285 strikes the anode 287 is shaped so that a central X-ray 392 of X-ray beam 282 originates at source location 280 and is directed toward the fulcrum point 402. Thus, as the electron beam 285 circumscribes a circular path along the surface 354, the central beam 392 is always directed toward the same location 402.

The material forming the surface 354 of the anode 287 is selected so that the radiation produced when electron beam 285 strikes the surface 354 has the desired energy characteristics. The radiation produced by bombarding a target material with an accelerated electron beam is known as Bremsstrahlung radiation. The characteristics of Bremsstrahlung radiation are determined primarily by the energy of the electron beam and the material composition of the target into which the electron beam is directed. In a preferred embodiment, the surface 354 which is bombarded by electron beam 285 is covered with a layer of tungsten metal.

The substrate 356 on which the tungsten surface 354 is placed may be copper or other suitable metal. A material with a high heat conductivity, such as copper, is particularly well suited for this application since significant heating of the target anode 287 occurs when the energy of the electron beam 285 is deposited in the anode. The copper substrate 356 provides a very efficient heat conductor for removing this heat from the locations 280 where electron beam 285 collides with the anode 287.

The radiation beam 282 produced in the collision of electron beam 285 with tungsten layer 354 exits the tube 200 through a window 370. The window 370 forms a portion of the vacuum envelope of the tube 200 in which the electron beam 285 propagates which allows the X-rays produced within the tube at the surface 354 to exit the vacuum portion of the tube with minimal loss of intensity and energy. Titanium is commonly used to form X-ray windows for X-ray tubes and is preferred in this embodiment for window 370. However, it will be understood that other materials could also be used to form the window 370.

During the X-ray inspection of a circuit board or other object 410, it is often advantageous to turn off the X-rays while the circuit board is being moved so that different regions of the board fall within the inspection area 400. It is desirable that the X-rays be turned on and off as rapidly as possible. Additionally, it is desirable to perform the ON/OFF cycling so that the X-rays produced during all of the ON portions of the cycles have substantially identical energy, intensity and optical characteristics. X-ray tube 200 accomplishes this rapid ON/OFF stabilized cycling of the X-rays by directing the electron beam 285 into the beam stop 360. This diversion of electron beam 285 prevents X-rays from exiting the window 370. Thus, radiation production directed toward the object 410 is stopped, i.e. turned off, while the object is being repositioned. Steering coils 281 provide a fast means for accomplishing this deflection of electron beam 285 into the beam stop 360. This method of turning off the X-rays enables the electron beam 285 and all other functions of the X-ray tube which affect the X-ray beam 282 characteristics to be left undisturbed during the ON/OFF cycling. Therefore, when the electron beam 285 is redirected to the anode 287 for the ON portion of the cycles, the characteristics of X-ray beam 282 are substantially unchanged from previous ON cycles.

The beam stop 360 is formed of a material which is highly attenuative of X-rays, for example, lead or copper. The thickness, location, and shape of the beam stop 360 are selected to prevent X-rays from exiting the tube 200 via the window 370 when the beam is directed into the beam stop. These parameters are easily determined by one skilled in the art of X-ray tube design.

Figure 5:
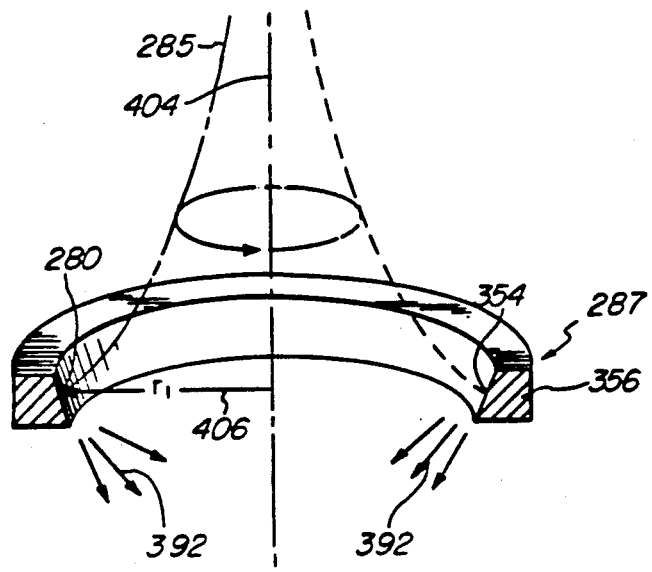
FIG. 5 is a cross-sectional view of the target anode of the X-ray tube shown in FIG. 4.

An enlarged cross-sectional view of anode 287 is shown in FIG. 5. In this preferred embodiment, the annular target surface 354 comprises a portion of a cone which is symmetric about an axis 404. The target anode 287 is mounted to the tube 200 such that the axis 404 of the cone coincides with the central Z axis of the tube 200. Thus, when the electron beam 285 is steered in a circular oscillation with the radius $r_1$ shown as 406, the effect is that of a moving spot source of radiation 280 having energy, intensity, and focus characteristics equivalent to conventional stationary radiation sources. It will be understood that other shapes for the anode 287 may be used which will produce equivalent results.

The X-ray source 200 thus provides a source of X-rays suitable for making high resolution X-ray images even when used in a geometry which magnifies the images. One such magnifying geometry is one wherein the object being imaged is located between an X-ray source and an X-ray detector such that the distance from the object to the X-ray source is less than the distance from the object to the X-ray detector. Additionally, source 200 has the capability of moving this source of X-rays in a circular pattern suitable for making laminographs. This circular motion is accomplished without sacrificing image resolution or speed of acquisition. Since the rotation of the radiation source is accomplished electronically, no moving parts are needed, thus eliminating vibrations and other undesirable characteristics of mechanical systems. An X-ray source having the above described characteristics is available from Kevex Corporation as Model No. KM160R. Other electrically steered moving X-ray sources are described in U.S. Pat. No. 4,075,489 entitled "Method and Apparatus Involving the Generation of X-Rays"; U.S. Pat. No. 4,352,021 entitled "X-Ray Transmission Scanning System and Method and Electron Beam X-Ray Scan Tube for Use Therewith"; and U.S. Pat. No. 2,319,350 entitled "X-Ray Tube and Apparatus." These patents are hereby incorporated herein by reference.

ROTATING X-RAY DETECTOR

Figure 6:
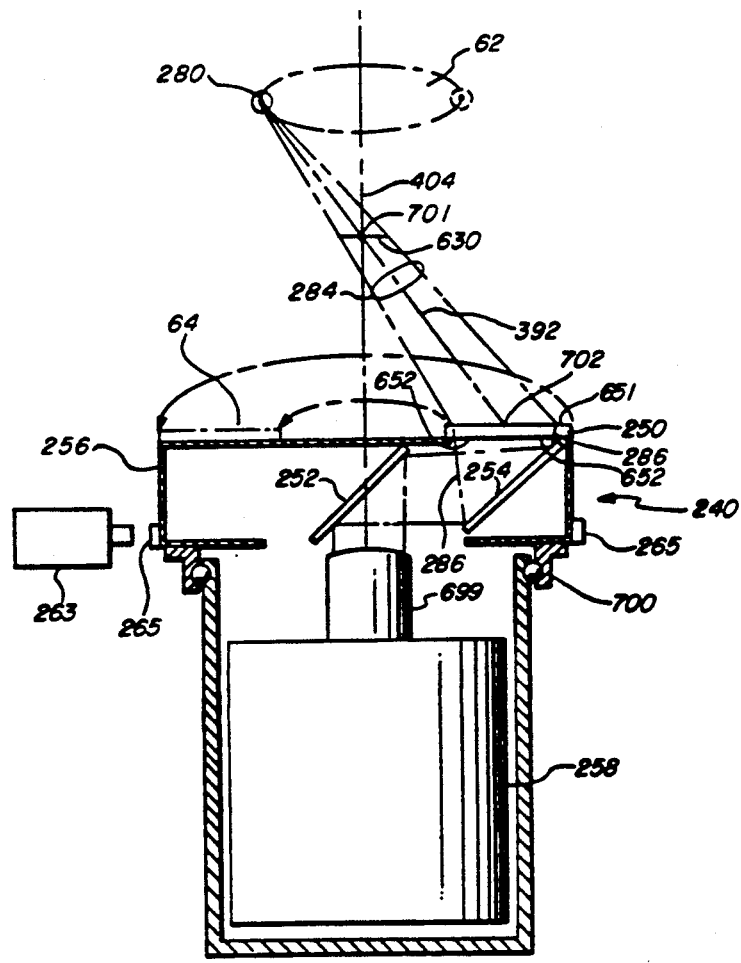
FIG. 6 is a cross-sectional view of the rotating X-ray detector and camera system.

Shown in FIG. 6 is an embodiment of the rotating X-ray detector system 240 discussed previously in connection with FIG. 3a and used in conjunction with the rotating X-ray source 280 to acquire cross-sectional images of an object 630. As shown in FIG. 6, an X-ray image of the object 630 is formed on the rotating fluorescent screen 250 by X-ray beam 284. Screen 250 converts these X-rays to optical signals 286 for detection by conventional optical devices. In the preferred embodiment, the optical signals 286 from rotating fluorescent screen 250 are detected by the closed circuit TV (CCTV) camera 258. Camera 258 converts the optical signals 286 to electrical signals for further processing by computer systems 270 and 272. The optical image formed on the screen 250 rotates with the screen. In order to eliminate the need for mechanical motion of the CCTV camera 258 which views the rotating optical image, the optical image is derotated within the rotating detector 240 by optical mirrors 252 and 254 so that the rotating optical images formed on the rotating screen 250 appear stationary as viewed by the camera.

The rotating X-ray detector 240 comprises the turntable 256 rotatably mounted about the axis 404 by a bearing 700. It is noted that the axis 404 is nominally the same axis about which the source of rotating X-rays 280 revolves. The fluorescent screen 250 is attached to the top of turntable 256. The two mirrors 252 and 254 are mounted within turntable 256 parallel to one another and at an angle of 45° with respect to axis 404. The mirror 252 is mounted in the center of turntable 256 so that it intersects the axis 404 near the center of the mirror. The mirror 254 is mounted within turntable 256 so that it faces both the first mirror 252 and the fluorescent screen 250. Fluorescent screen 250 and mirrors 252 and 254 are attached to turntable 256 so that the turntable, mirrors and screen rotate about axis 404 as a single unit. This arrangement of mirrors, turntable, and screen forms an optical derotation assembly for optical images formed on the screen 250 when the detector 240 is rotated about the axis 404.

An X-ray shadow image of the object 630 is formed on the fluorescent screen 250 when the X-ray beam 284 strikes the screen. The fluorescent screen 250 functions as an X-ray to optical converter. For example, when X-rays 284 strike the surface 651 of the screen 250 which faces the X-ray source 280, visible light 286 is emitted from the screen surface 652 opposite the X-ray source 280. Optical signals 286 emitted from the fluorescent screen surface 652 are reflected by the two parallel mirrors 252 and 254 into a lens 699 attached to the closed circuit TV camera 258.

The fluorescent screen 250 is mechanically rotated at a uniform angular velocity about the axis 404 in plane 64 which is substantially parallel to plane 62 defined by the circular motion of the moving spot source of radiation 280. The mirrors 252, 254 reflect the optical image from the rotating fluorescent screen into the stationary camera system 258 through the lens 699 so that the rotation of the image in the plane 64 is not apparent to the camera 258. This mirror arrangement has been previously described in U.S. Pat. No. 2,998,511 entitled "Tomoscope."

As a result of the fixed mounting of the fluorescent screen 250 to the rotating turntable 256, successive images of object 630 formed on the screen have different orientations with respect to the screen as it traverses its circular path about the axis 404. Thus, in order to avoid blurring of the image caused by the movement of the image with respect to the screen, it is desirable that the fluorescence of a point on the screen surface be suppressed abruptly after that point is no longer hit by an X-ray. In a preferred embodiment, the fluorescent screen 250 comprises praseodymium-doped gadolinium oxysulfide, $Gd_2O_2SiPr$. Praseodymium-doped gadolinium oxysulfide is a scintillation material which is "fast" enough to prevent blurring due to motion of the image with respect to the screen and also provides sufficient light output for detection by the camera system 258.

Alternatively, "slower" screens may be used, for example, a screen which comprises a cadmium tungstate scintillation material. However, rotatably mounted to the turntable 256 such that an image of object 630 formed on the screen remains stationary with respect to the screen. Such a motion may be accomplished, for example, by a set of gears which superimposes a circular motion of the screen with respect to the turntable in synchronization with the rotation of the turntable about the axis 404.

An alternative embodiment (not shown) for the rotating X-ray detector 240 which forms an optical derotation assembly replaces the two flat mirrors 252,254 with a suitably bent bundle of image conductors, e.g., optical fibers, which are coupled to the fluorescent screen 250 and rotate in unison with the screen. The image conductors transmit the image from the fluorescent screen 250 to a position centered on the axis of rotation 404, to the same effect as the two parallel mirrors shown in FIGS. 3a and 6. These image conductors may comprise optical fibers, electron conductors or equivalent devices.

CROSS-SECTIONAL IMAGE FORMATION

As previously discussed, a cross-sectional image of object 630 is formed on screen 250 as the screen 250 and X-ray source 280 synchronously rotate about axis 404. The blurring effects of the laminography method and image resolution are maximized when the cross-sectional image is acquired during a full rotation of the screen 250 and source 280 about the axis 404. The camera system 258 detects the development of the cross-sectional image on the fluorescent screen 250 by means of the optical derotation assembly comprising mirrors 252 and 254.

Since the fluorescent screen 250 may not emit high intensity optical signals, it is often advantageous to detect the optical signals 286 with a high sensitivity, low light level device. Use of a low light level detection device thus improves the detected image quality by detecting a larger portion of the optical signals 286 emitted from the fluorescent screen 250 during a single rotation of the screen. Many low light level camera systems incorporate an image intensifier as part of the camera system to improve the low light level sensitivity. One particular system is known as a silicon intensified target (SIT) camera and is capable of detecting extremely low levels of light. SIT camera systems are well known and readily available. A preferred embodiment of the present invention utilizes a SIT camera system which is based upon the RCA Model No. 4804BHP2-12 SIT tube.

In a preferred embodiment, one cross-sectional image is acquired in approximately 0.1 seconds during the rotation of the fluorescent screen 250 about the axis 404 at the rate of approximately 600 revolutions per minute. During one complete revolution, three video frames, each frame having a duration of 1/30 of a second, are collected by the camera 258. The three video frames are communicated from the camera 258 to master computer 270 (shown in FIG. 3a) where the three frames are averaged together, thus forming a digital representation of the cross-sectional image of the object 630 formed on the fluorescent screen 250 during a single rotation of the screen 250 about the axis 404. Alternatively, the camera 258 may be connected to a CRT, so that the cross-sectional image can be viewed directly.

SOURCE/DETECTOR SYNCHRONIZATION

Figure 7:
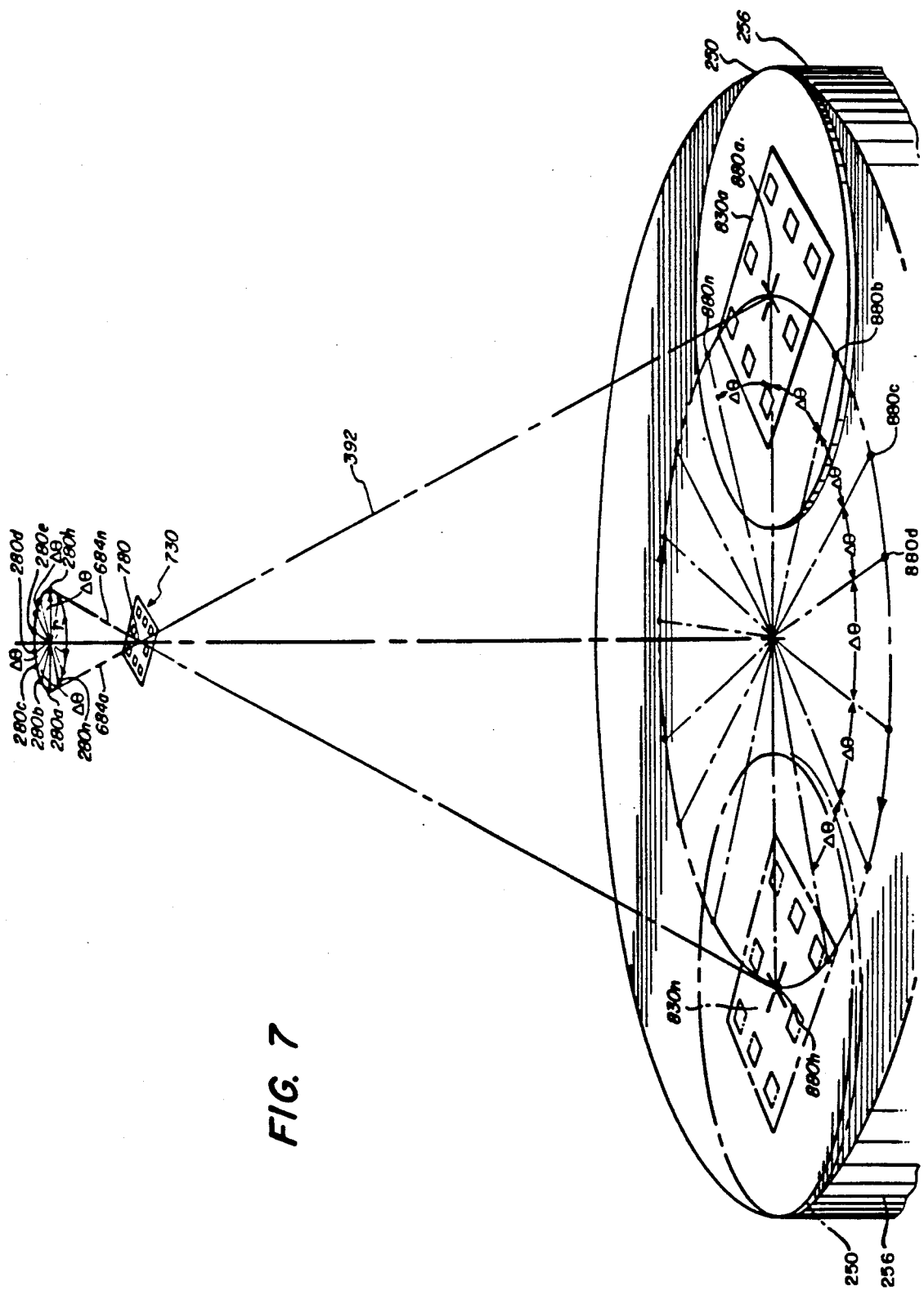
FIG. 7 is a schematic diagram illustrating the calibration procedure for synchronizing the X-ray source and detector positions.

Formation of a high resolution laminographic cross-sectional image depends upon the precise alignment and synchronization of the circular motions of the radiation source 280 and detector screen 250. As illustrated in FIG. 7, proper alignment and synchronization are achieved when central X-ray 392 from source 280 passes through a fixed point 780 lying on the axis 404, such that the central X-ray 392 is always directed to a single point 880 on the surface of detector screen 250. For the configuration shown in FIG. 7, this is clearly achieved when the angular positions of the source and detector screen, relative to a fixed reference position, are separated by 180°.

The preferred alignment and synchronization of the source 280 and detector screen 250 are maintained by the feedback system 260 shown in FIG. 3a. The position of the rotating turntable 256, upon which the X-ray detector screen 250 is mounted, is monitored by the sensor 263. The turntable position is communicated to the feedback system 260, which supplies drive signals corresponding to the position of the turntable to the electron beam deflection coils 281. The drive signals control the position of the X-ray source 280 such that the source 280 and screen 250 are always in alignment as the turntable rotates about the axis 404. In this manner, the feedback system maintains the precision geometry necessary for the production of high resolution cross-sectional images. This system compensates for alignment inaccuracies of the X-ray tube 200 and rotating X-ray detector 240; machining, mounting and fabrication inaccuracies and defects of the target anode 287 and its surface coating 354; aberrations, such as astigmatism, in the electron beam 285 path through the X-ray tube; and variations in the rotational velocity of the rotating turntable during image formation.

Figure 8:
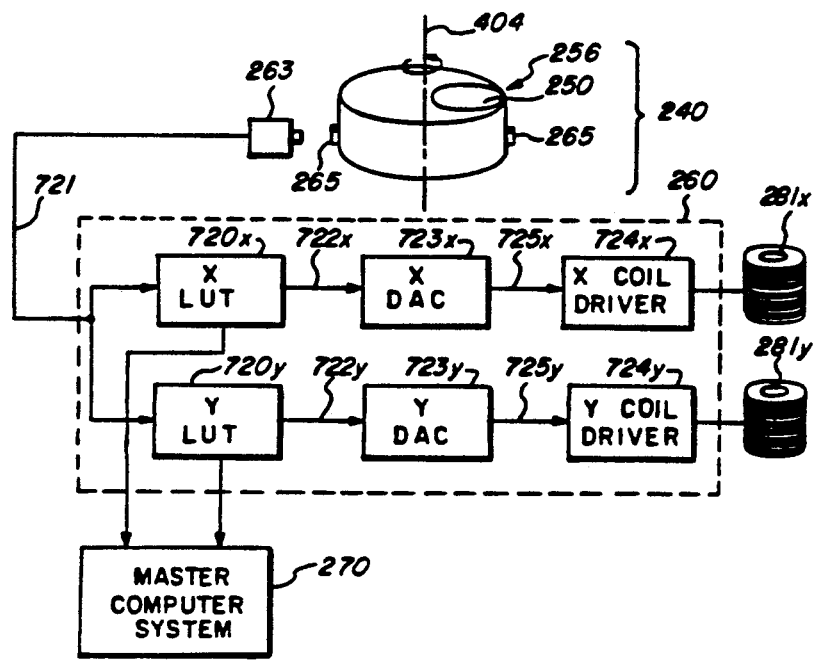
FIG. 8 is a schematic block diagram for the feedback control system used for the synchronization of the X-ray source and detector motions.

A detailed block diagram of feedback system 260 is shown in FIG. 8. Feedback system 260 comprises X and Y look-up tables (LUTs) 720X and 720Y, respectively, X and Y digital-to-analog converters (DACs) 723X and 723Y, respectively, and X and Y coil drivers 724X and 724Y, respectively. The LUTs 720X and 720Y are preferably solid state, digital random access memories (RAM). The feedback system links the rotating X-ray detector 240 to the X-ray tube deflection coils 281 under control of the master computer system 270.

As rotating X-ray detector 240 revolves about axis 404, the position sensor 263 detects the angular position of the detector 240 from the position encoder 265. The detected angular position is converted to X and Y address signals which correspond to the angular position of the detector. The address signals are communicated to the X and Y LUTs 720X, 720Y via a communication line 721. By means of a source/detector alignment calibration procedure, X and Y calibration data are determined and stored in the X and Y LUTs for each angular position of the detector. Thus, there exists a one to one correspondence between the X and Y addresses from the encoder and the X and Y calibration data in the LUT's. The X and Y calibration data are retrieved from the LUT's in the form of electronic digital signals. The electronic digital signals are transmitted from the X and Y LUTs to the X and Y DACs 723X and 723Y, respectively, via communication lines 722X and 722Y. The DACs convert the digital signals into analog electrical signals which travel via lines 725X and 725Y to the coil drivers 724X and 724Y. The coil drivers amplify their respective analog input signals and apply resulting output signals via lines 726X and 726Y to the coils 281X and 281Y, respectively, to achieve the precise deflection of the electron beam 285 required for proper alignment of the source and detector. The electron beam is deflected through interaction with magnetic fields generated by the application of the output signals to the coils 281. As the electron beam traverses the magnetic fields, it is deflected, thus moving the position of the X-ray source spot 280 on the anode 287. The distance the spot moves is proportional to the magnitude of the drive signals as determined by the calibration data.

The LUT calibration data are determined using the calibration configuration schematically illustrated in FIG. 7. A test pattern 730 is positioned between the X-ray source 280 and detector screen 250 such that test pattern 730 intersects the axis 404 at location 780. A conventional X-ray shadowgraph image 830 of test pattern 730 is formed on screen 250. The optical representation of X-ray image 830 on the screen is viewed by the camera 258 (See FIG. 3a). An electrical representation of the optical image is output from camera 258 by means of electrical signals on line 276 to master computer 270 and image analysis computer 272. The electrical signals on line 276 are digitized by computer 270 and stored in the memory of computer 270 in digital format.

Figure 9A:
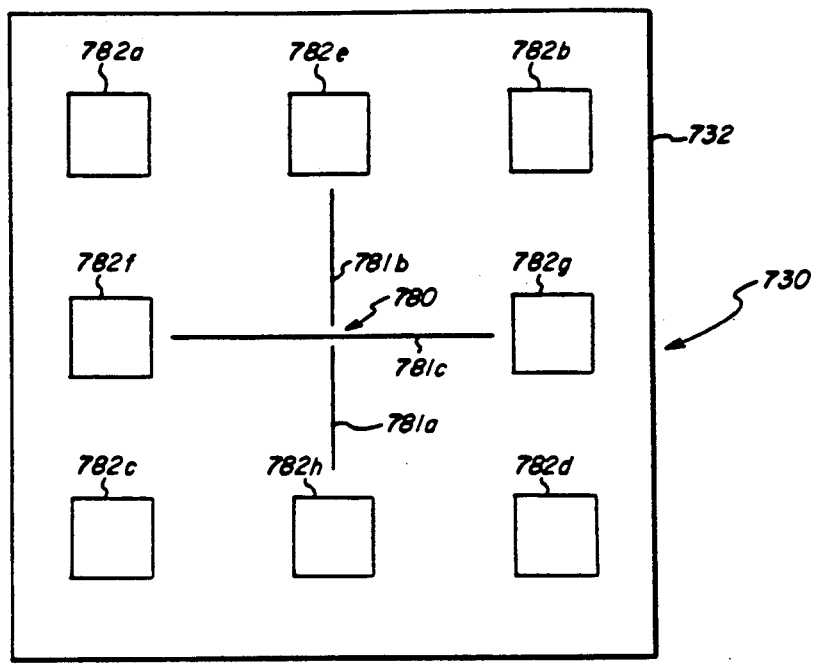
FIG. 9a illustrates a test fixture for use in the calibration procedure shown in FIG. 7.

A preferred embodiment of test pattern 730, shown in FIG. 9a, comprises a foundation 732 of material such as plastic, which is relatively transparent to X-rays. Foundation 732 is approximately 0.5×0.5 inch in length and width, and approximately 0.1 inch thick. At a center location 780 on foundation 732 are mounted three pieces of 0.001 inch diameter tungsten wire 781a, 781b and 781c, oriented such that wire 781c intersects the center location 780. Wires 781a and 781b are mounted to foundation 732 so that they are on opposite sides of wire 781c, and so that a line connecting wires 781a and 781b also intersects center location 780. Thus, wires 781a, 781b and 781c form a fiducial crosshair 781 having its center at location 780. Mounted around the crosshair 781 are eight markers 782 made of lead or other X-ray opaque material. Lead markers 782a through 782d are approximately 0.0625 inch square and 0.004 inch thick, and are located near the four corners of the foundation 732. Lead markers 782e through 782h are approximately 0.0625 inch square and 0.008 inch thick, and are positioned intermediate the markers 782a through 782d.

Figure 9B:
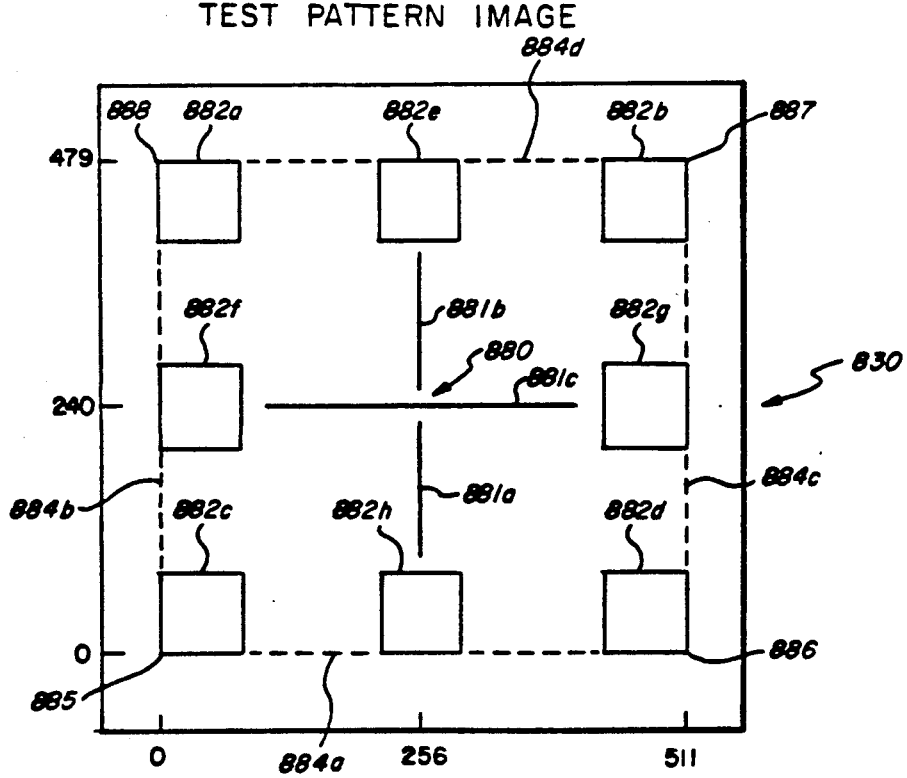

A representation of a typical X-ray shadowgraph image 830 of test pattern 730 is shown in FIG. 9b. Lead markers 782a through 782h form image regions 882a through 882h, respectively, of image 830. The center 780 of test pattern 730 is represented by image center 880. Likewise, tungsten wires 781a through 781c form image regions 881a through 881c, respectively.

A portion of image 830 represented by the dotted lines 884a through 884d forms a rectangular region of interest (ROI) 884 which surrounds the images of lead markers 882 and tungsten wires 881. Region of interest 884 is stored in the computer 270 in digital format. As is well known, digitally stored images comprise an array of pixels, each pixel representing a small portion of the image. Specifically, region of interest 884 is divided into a pixel grid comprising 512 columns along border 884a and 480 rows along border 884b. Each pixel in the grid may be represented by its corresponding column and row designation. For example, the lower left corner 885 of region of interest 884 is represented by the pixel (0,0). Similarly, corner 886 is represented by pixel (511,0), corner 887 is represented by pixel (511,479) and corner 888 is represented by pixel (0,479). The center location 880 is represented by pixel (256,240). In one embodiment, the distance between corners 885 and 886 of the image 830 corresponds to approximately 0.400 inches on the test pattern 730. Likewise, the distance between corners 885 and 888 of the image corresponds to approximately 0.375 inches on the test pattern.

Determination of the calibration data for the X and Y LUTs is performed either manually or automatically using the test pattern 730. Referring again to FIGS. 3a and 7, an initial alignment of the X-ray source 280, test pattern 730, turntable 256 and camera 258 is performed manually. First, the test pattern 730 is positioned so that the center 780 intersects the axis 404. The X-ray tube 200, turntable 256 and camera 258 are then mechanically aligned so that the test fixture image 830, formed on the screen 250, is continuously within the field of view of the camera throughout a complete revolution of the source 280 and turntable 256 about the axis 404. After the system is thus mechanically aligned, the turntable 256 is positioned at an initial angular position defined as $\theta=0°$. In this initial position, the center pixel (256,240) of the digital image detected by the camera and stored in the computer corresponds to a location 880a on the screen 250. The source 280 is positioned at a location 280a which corresponds to an angular position of approximately $\theta=180°$, thus placing the test pattern image 830 within the field of view of the camera. If the image center 880 of the test pattern image 830 does not fall within the center pixel (256,240), then the X and Y deflection values are adjusted to change the position 280a of the source 280, which in turn changes the location of the image center 880 on the screen 250. The deflection values are adjusted until the image center 880 is caused to be precisely located at center pixel location (256,240). These deflection values are then stored in the LUT's 720 as the calibration data for the turntable 256 position $\theta=0°$. Turntable 256 and screen 250 are then moved to a new angular position corresponding to an angle $\theta=\Delta\theta$. Source 280 is moved to a position 280b corresponding to an angular position of approximately $\theta=\Delta\theta+180°$, thus placing the test pattern image 830 within the field of view of the camera. If the image center 880 of the test pattern image 830 does not fall within the center pixel (256,240), then the X and Y deflection values are adjusted to change the position 280b of the source 280 so that the image center 880 is again caused to be precisely located at center pixel location (256,240). These deflection values are then stored in the LUT's as the calibration data for the turntable 256 position $\theta=\Delta\theta$. This procedure for determining the LUT calibration data is continued in increments of $\Delta\theta°$ until the source 280 and turntable 256 have completed one revolution about the axis 404.

The LUT calibration data determined for positions 280a, 280b, 280c, . . . , 280n of the source are used to determine the formula representing a circle of radius r as a function of angular position $\theta$. The radius r is the nominal radius of the path followed by the rotating source 280. This formula is then used to calculate calibration data for locations of the source intermediate the locations 280a, 280b, 280c, . . . , 280n.

Figure 10A:
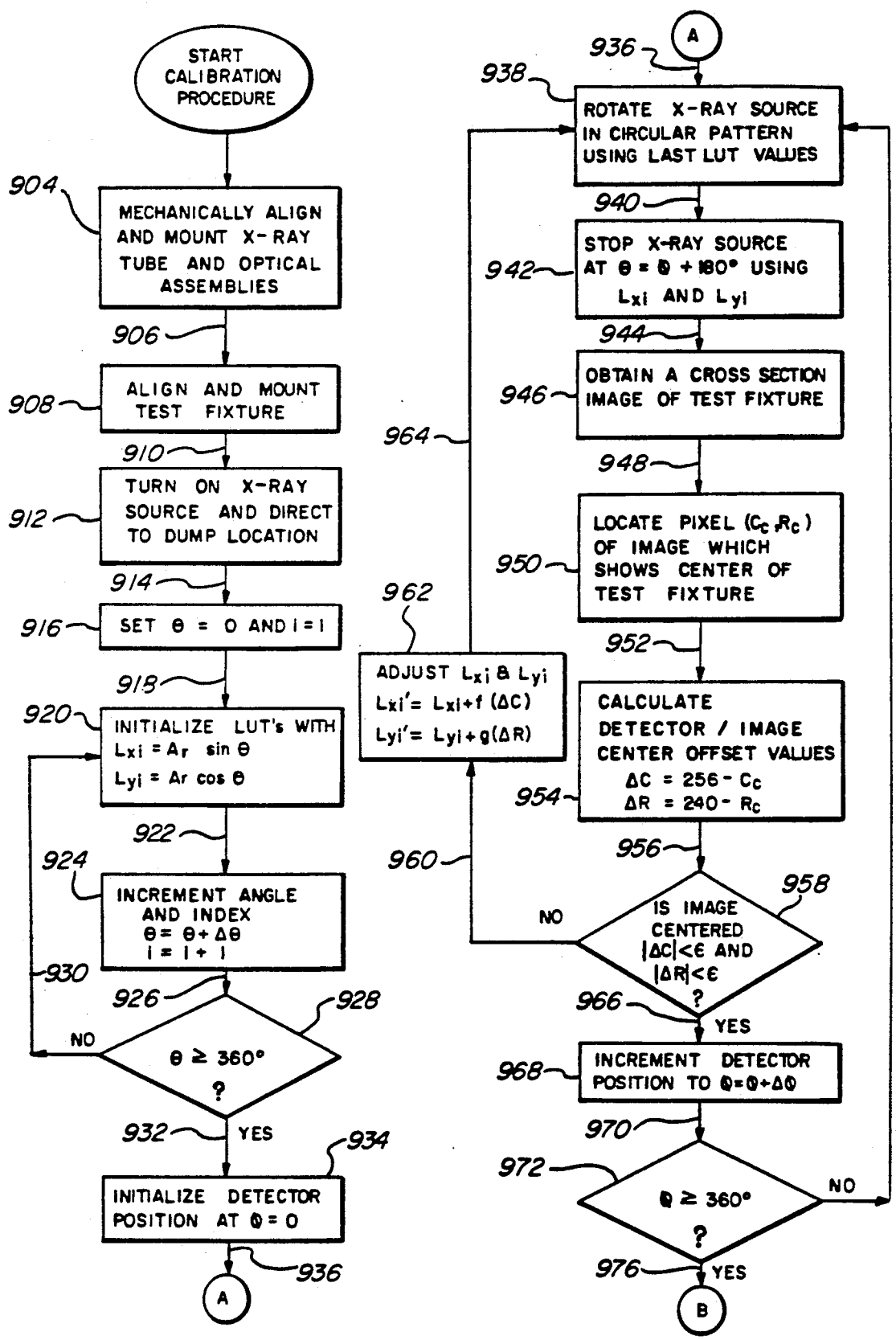
FIG. 10a is a flowchart of a procedure used to calibrate the synchronization of the X-ray source and detector positions.
Figure 10B:
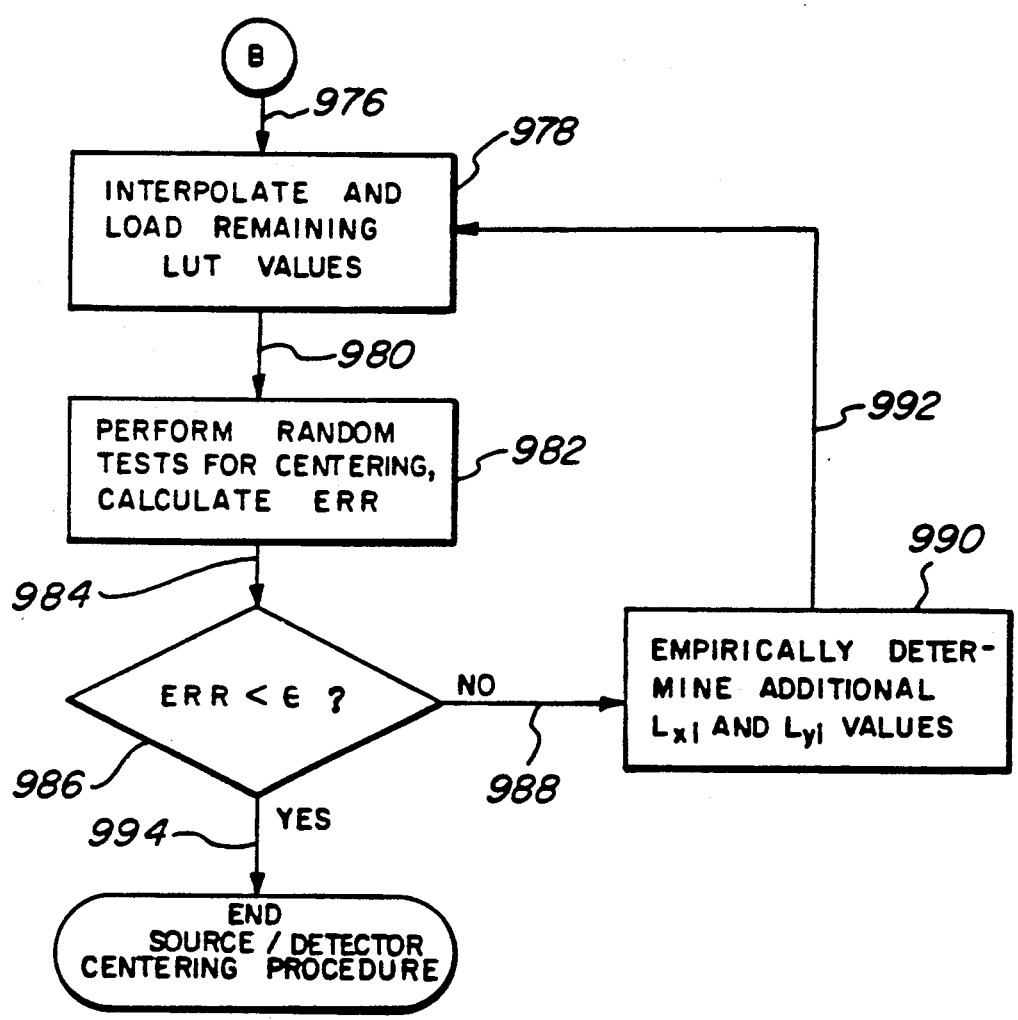

FIG. 10 illustrates a basic flow chart of the logical sequence of steps performed by the calibration procedure to determine the X and Y calibration data which are stored in the X and Y LUTs 720 for controlling the deflection coils 281. First, as previously described, the mechanisms of the invention, as shown in FIG. 3a, including the X-ray tube 200, turntable assembly 256 and XYZ positioning table 230 are assembled and mounted in approximate alignment. Next, test pattern 730 is mounted to the XYZ positioning table and moved by the XYZ positioning table to a position such that the center location 780 of the test pattern 730 coincides with the point 780 represented by the intersection of the central axis 404 and the nominal center X-ray 392 from the X-ray source 280 (See FIG. 7).

The step of mechanically aligning the X-ray tube 200 and optical assemblies is represented by an activity block 904 in FIG. 10. Control is passed from activity block 904 via a path 906 to an activity block 908, wherein the test fixture 730 is mounted and aligned on the positioning table. Control then passes via a path 910 to an activity block 912 wherein the X-ray source is turned on and the electron beam is directed to a beam dump location. This allows the X-ray tube to stabilize without subjecting the test pattern and detector to X-rays. Control proceeds via path 914 to an activity block 916 wherein the angular position variable $\theta$ and an address indexing variable i are initialized at $\theta=0°$ and i=1, respectively. Control is passed from activity block 916 to activity block 920 via a path 918. Activity block 920 represents the initialization of the LUTs with initial approximations given by $$L_{xi}=A_r \sin\theta \tag{1}$$

$$L_{yi}=A_r \cos\theta \tag{2}$$

where $A_r$ is proportional to the approximate radius of the rotating source 280 and i is the LUT address which contains deflection data corresponding to the angular position $\theta$. In activity block 924, reached via path 922 from block 920, the angular position $\theta$ is incremented by an amount $\Delta\theta$ and the index i is incremented by 1. In one preferred embodiment, the angular increment $\Delta\theta$ is approximately 0.022°, corresponding to approximately 16,384 angular positions in one revolution. In this embodiment, the X and Y LUT's each have at least 16384 address locations for the storage of deflection data corresponding to each discrete angular position, and the addressing index i takes on integral values ranging from 1 to at least 16384. Control then passes via path 926 to decision block 928. In decision block 928, the value of $\theta$ is checked to see if it is greater than or equal to 360°. If $\theta$ is not greater than or equal to 360°, then control returns to block 920 via path 930. If $\theta$ is greater than or equal to 360°, then control passes via path 932 to activity block 934. The steps from 920 through 928 form a loop wherein all of the available LUT addresses are loaded with initial deflection values which will cause the electron beam to circumscribe a circular path upon the anode of the X-ray tube. In the embodiment having 16,384 discrete angular positions, the steps 920 through 928 will be executed approximately 16,384 times.

Upon completion of the LUT initialization process, control passes via path 932 to activity block 934, wherein the detector is positioned at an initial reference location defined as $\phi=0°$. Control is then transferred via path 936 to activity block 938, wherein the current data $(L_{xi}, L_{yi})$ stored in the LUT's are used to control the rotation of the X-ray source. When activity block 938 is entered via path 936, the current data in the LUT's are the initial values calculated in accordance with equations (1) and (2) and represent an initial approximation of the final values to be calculated by the below described calibration procedure.

Determination of the LUT calibration data proceeds via a path 940 to activity block 942. In block 942, the rotating X-ray source 280 is stopped at the angular position $\theta$ which is approximately equal to $(\phi+180°)$, where $\phi$ is the angular position of the X-ray detector. For example, when the detector is at the initial position $\phi=0°$, then the X-ray detector is positioned at angular position 180° in block 942. In the embodiment having 16,384 angular positions and corresponding LUT addresses, the deflection values stored in LUT memory locations $L_{x8192}$ and $L_{y8192}$ will produce the deflection of the electron beam to the location on the anode corresponding to an angular position of the X-ray source of 180°.

Subsequent to stopping the rotating X-ray source at angle $\theta$ in activity block 942, control is passed via line 944 to activity block 946. In activity block 946, a cross-sectional image 830 of test pattern 730 is obtained and stored in a digital image memory. In a preferred embodiment, the image memory comprises a pixel grid having 512 columns and 480 rows.

A path 948 transfers control from activity block 946 to an activity block 950, wherein the pixel(s) $(C_c, R_c)$ containing the location of the image center 880 of image 830 are located. $C_c$ and $R_c$ are the column and row designations respectively, of the image pixel containing the center of the image, and may be identified manually or automatically by means of computer analysis techniques.

The image center pixel position $(C_c, R_c)$ determined in activity block 950 is transferred to activity block 954 via path 952, wherein the relative offset of the image center from the detector center is calculated according to the following equations.

$$\Delta C = 256 - C_c \qquad (3)$$

$$\Delta R = 240 - R_c \qquad (4)$$

$\Delta C$ and $\Delta R$ represent the distance by which the center of the test pattern image $(C_c, R_c)$ is offset from the center of the digital image defined as pixel (256,240).

The $\Delta C$ and $\Delta R$ values calculated in activity block 954 are transferred via path 956 to decision block 958, wherein $\Delta C$ and $\Delta R$ are compared to the value zero. If $\Delta C$ or $\Delta R$ is not substantially equal to zero, i.e., if their absolute values are not less than some arbitrarily small number, $\epsilon$, then the test pattern image center is not coincident with the digital image center and control is passed via path 960 to activity block 962 where the LUT calibration data are adjusted accordingly.

In activity block 962, the LUT calibration data $L_{xi}$ and $L_{yi}$ are adjusted in accordance with the following equations.

$$L_{xi}' = L_{xi} + f(\Delta C, \Delta R) \qquad (5)$$

$$L_{yi}' = L_{yi} + g(\Delta C, \Delta R) \qquad (6)$$

Mathematical functions $f(\Delta C, \Delta R)$ and $g(\Delta C, \Delta R)$ are used to calculate the magnitude of adjustments for the LUT values $L_{xi}$ and $L_{yi}$ respectively, which will reduce the centering errors $\Delta C$ and $\Delta R$. The values $L_{xi}$ and $L_{yi}$ in the LUT's are replaced with the adjusted values $L_{xi}'$ and $L_{yi}'$ respectively. These adjusted LUT values are transmitted to the activity block 938 via line 964 and a first loop comprising the steps 938, 942, 946, 950, 954, 958, and 962 is re-executed until the image center is substantially coincident with the digital image center. When the image is centered, $\Delta C$ and $\Delta R$ are substantially equal to zero and control passes from decision block 958 via path 960 to activity block 968.

In block 968, the detector position is incremented by the amount $\Delta \phi$ to the next angular position $(\phi + \Delta \phi)$. The new angular position of the detector is passed via path 970 to decision block 972 to determine if the new angle $\phi$ is greater than or equal to 360°. If $\phi$ is less than 360°, then control passes via path 974 to activity block 938. A second loop comprising the first loop and additional steps 968 and 972 is re-executed until the detector has completed one revolution, i.e., when $\phi$ is greater than or equal to 360°.

In a preferred embodiment, the angular increment $\Delta \phi$ is selected to be substantially larger than the angular increment $\Delta \theta$ between successive entries in the LUT's so that a calibration for a complete revolution can be calculated in a short period of time. For example, if the increment $\Delta \phi$ is equal to 10°, then a complete revolution can be calculated with 35 executions of the second loop. The remaining LUT values corresponding to positions intermediate the 36 calculated positions are determined by interpolating between the adjacent calculated values as indicated in activity block 978. Control is then passed to activity block 982 via path 980 for random testing of the centering of the image.

In activity block 982, random angular positions are selected where the accuracy of the centering is determined. A centering error, ERR, is calculated which reflects the cumulative error of all of the selected positions. The centering error value is passed via path 984 to decision block 986 wherein the value is compared to zero or some other predetermined value. If ERR is not substantially zero, then control passes via path 988 to activity block 990.

In activity block 990, additional LUT values $L_{xi}$ and $L_{yi}$ which are located intermediate the first 36 values determined are empirically by re-executing the second loop for 36 additional values. For example, if the values determined in the first execution of the second loop were for the angles $\phi_1 = 0, 10, 20, 30, \ldots, 340$ and 350 degrees, then the intermediate angles determined in the second execution of the second loop would be $\phi_2 = 5, 15, 25, 35, \ldots, 345$ and 355 degrees.

A third loop comprising steps 978, 982, 986 and 990 is re-executed until the error value is substantially zero or until all of the LUT locations have been empirically determined. Control is then passed via path 994 to the end of the calibration procedure.

In a preferred embodiment, the total number of positions represented by the LUTs is approximately 16,000. The starting and stopping of the rotation of the electron beam indicated in blocks 938 and 942 between successive calibration locations serves at least two functions. First, excessive heating of the target anode on the X-ray tube is prevented by because the rotating electron beam does not strike any one spot on the anode for an extended period of time. Second, hysteresis effects in the steering coils are automatically compensated by continuous passage through complete hysteresis cycles. It will be understood that the above calibration procedure can either be performed manually under operator control or automatically under computer control.

Due to the finite amount of time required for the signals from the position encoder on the rotating detector to arrive at the LUT and the corresponding LUT values to drive the deflection coils on the X-ray tube, there may be a time differential or lag between the time the position of the rotating detector is sensed and transmitted to the LUT's and the time the corresponding deflection data is transmitted from the LUT's to the X-ray tube deflection coils. At very slow or zero rotation, this lag is insignificant. However, as the rotation rate increases, the lag becomes greater and greater. This lag may be compensated for by a phase offset inserted between the position encoder and the LUT. The optimum phase offset is determined by varying the offset while evaluating the focus of the image 830. For other than optimum offsets, the image will be blurred. The optimum offset will correspond to the sharpest image while the detector is rotating at a constant speed.

It will be understood that other calibration procedures may be used to synchronize the rotation of the X-ray source and detector.

COMPUTER CONTROL AND ANALYSIS SYSTEM

Figure 11:
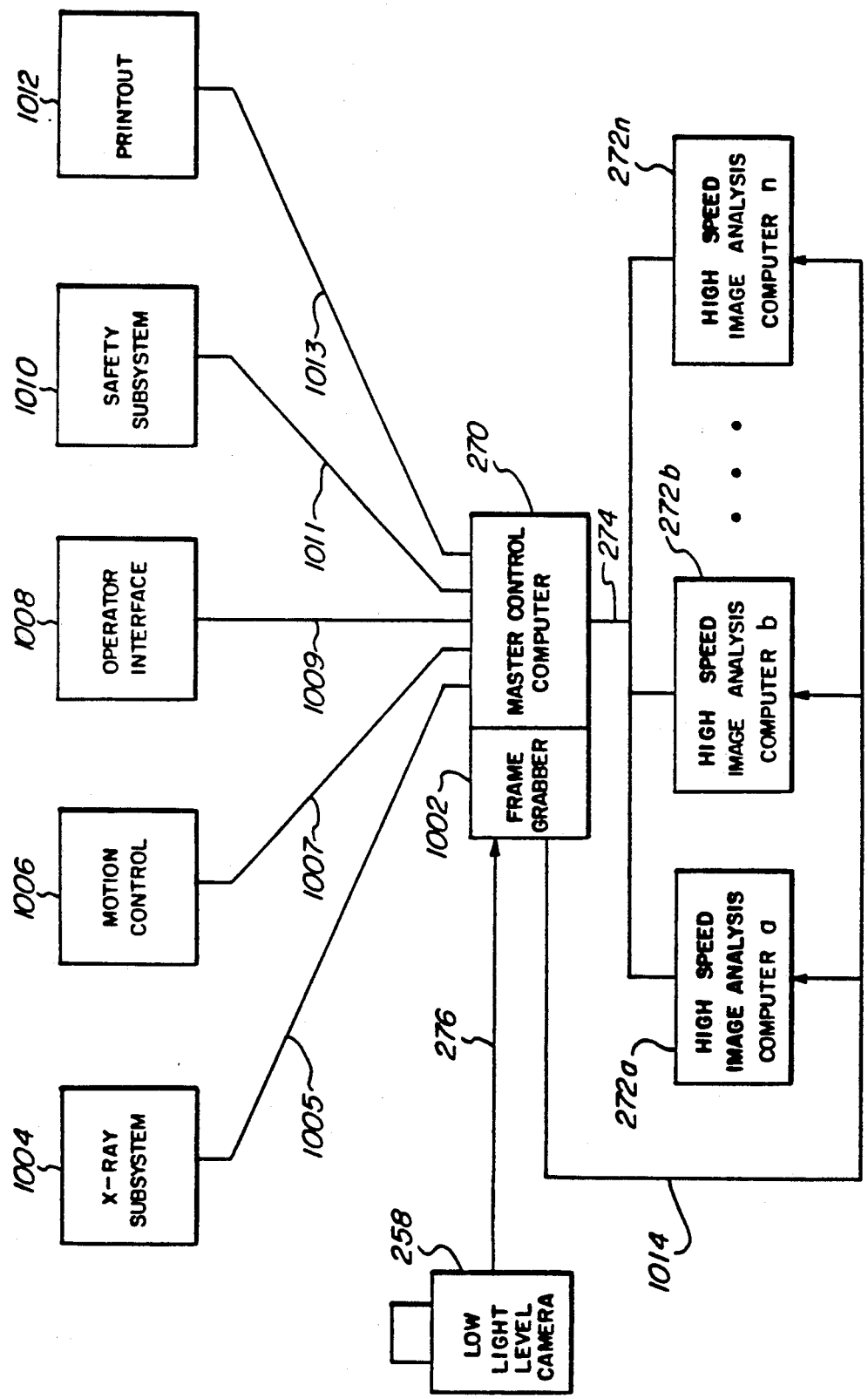
FIG. 11 is a block diagram of the computer control and analysis system.

FIG. 11 is a block diagram of the computer control and analysis system architecture for the automated laminography inspection system of the present invention. The computer system is centered about the master control computer 270. A video frame grabber 1002 is incorporated into the computer 270 via a plug-in board. The low light level camera 258 is connected to master computer 270 via the line 276. A variety of subsystems, including X-ray 1004, motion control 1006, operator 1008, safety 1010, and printout 1012 communicate with the master computer via communication lines 1005, 1007, 1009, 1011 and 1013, respectively. Multiple high speed image analysis computers 272a, 272b, 272n, also called "analysis engines", communicate with the master computer via the data network 274. These communications take the form of "messages" that are passed between the master computer and the analysis engines via the data network 274. The analysis computers 272 also communicate with the frame grabber 1002 via a communication line 1014. In a preferred embodiment, each analysis computer 272 comprises a COMPAQ® 386 processor board with an 80386 CPU, 5 megabytes of main RAM memory and a video frame grabber memory. The master computer 270 also comprises a COMPAQ® 386 processor board with an 80386 CPU. The analysis computers 272 are connected to the master computer 270 by a standard SCSI network.

In operation, the master computer 270 controls the operation of the inspection system through the various subsystems 1004 through 1012. The master computer also controls the acquisition and analysis of the laminographic images from which is derived a measure of the quality of the item under inspection. The master computer automatically controls the operation of the invention in two ways. First, a programmed sequence of movements is executed to acquire digital cross-sectional images Second, a programmed analysis procedure automatically examines and interprets the digital cross-sectional images. The analysis of one image may be performed simultaneously with the acquisition of a second image. The analysis performed by the master computer system results in an output data listing which categorizes the various defects and other conditions that were detected in the item under examination.

Specifically, for the inspection of solder joints on printed circuit boards, as illustrated in FIGS. 3a and 3b, the computer controls the motion of the XYZ positioning table 230 to which the circuit board 210 is mounted. Often the area contained within one cross-sectional image, for example 0.400 inch×0.375 inch, is smaller than the total area of the circuit board or other item to be inspected. In this case, the item is logically represented by multiple XY fields of views which, when combined, include the total inspectable area of the circuit board. The master computer positions each XY field of view for inspection by issuing appropriate motion commands to the XYZ positioning table. After the first XY field of view is in position for inspection, the resulting cross-sectional image is acquired and integrated in the camera. The video signal of the image is then transmitted from the camera to the high speed image analysis computer 272. The circuit board may also be moved to specific Z locations in order to bring different planes of the solder joints into focus in the resulting cross-sectional images.

The preferred scan sequence for a circuit board is to collect all of the required Z level images for a fixed XY location, then move to the next XY location and collect all of the required Z level images for that location. This step and repeat sequence iterates until all necessary areas and levels of the board have been imaged and analyzed.

The fully automated inspection of all solder connections on a circuit board, performed under the control of the master computer, utilizes a preprogrammed inspection routine, custom tailored for the specific circuit board design being inspected. The board is scanned, and each solder connection is examined through the acquisition and analysis of cross-sectional images.

Figure 12:
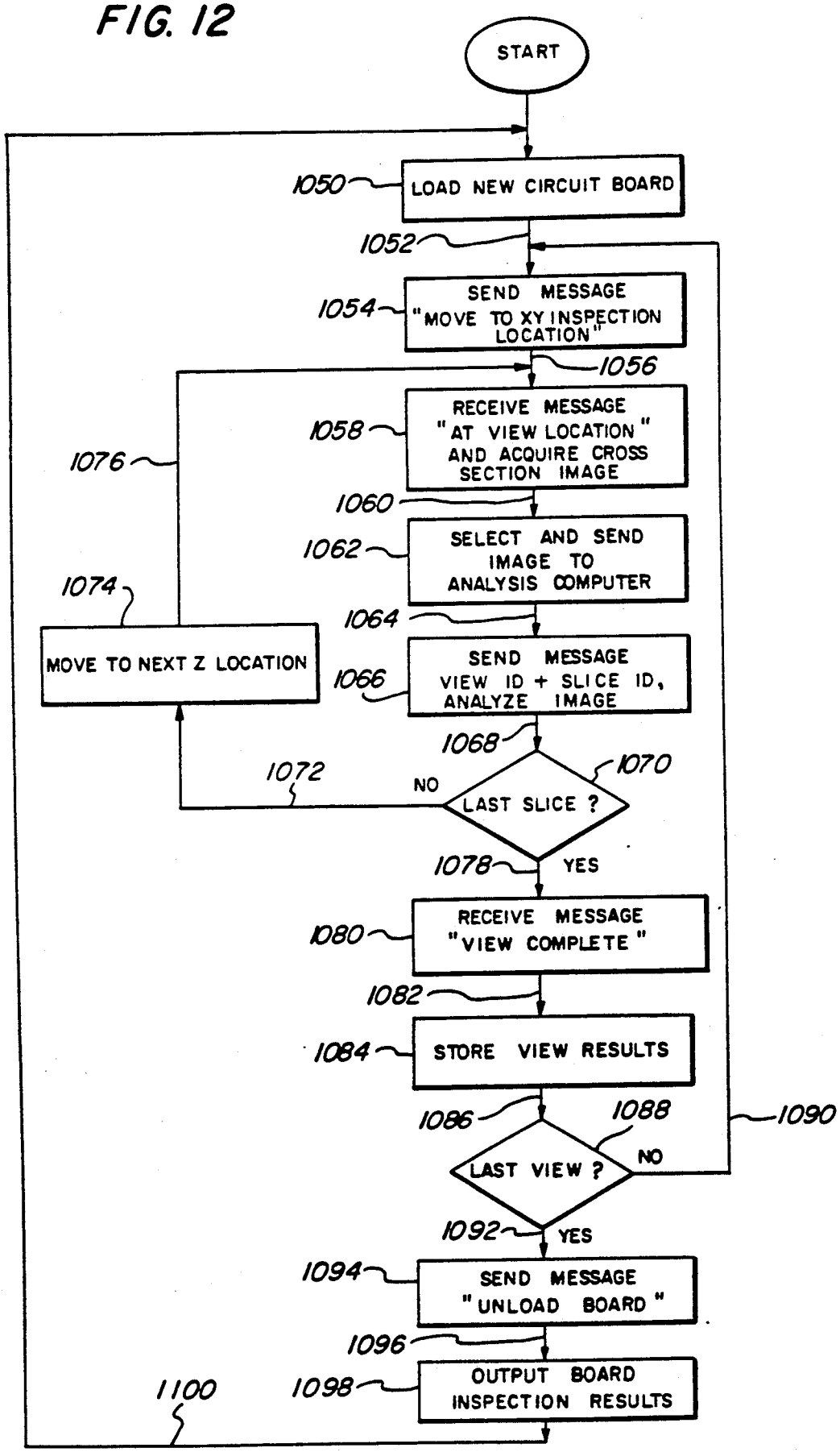
FIG. 12 is a schematic flowchart of the operation of the master control computer, showing the automated sequence of operations.

A flow chart illustrating the steps of this automated inspection routine is shown in FIG. 12. Beginning in activity block 1050, a circuit board for inspection is inserted into the load/unload port 292 of the invention (see FIG. 3c). Control is then transferred via path 1052 to activity block 1054 wherein the master computer sends a message to the XYZ positioning table which causes it to move the circuit board into the first XY view location.

Proceeding via path 1056, the routine enters a first loop comprising activity blocks 1058, 1062, 1066, 1070 and 1074. In activity block 1058, the master computer receives a message that the board is at the first view location. The master computer then controls the X-ray and detector subsystems such that a cross-sectional image of the board at that location is acquired. After the cross-sectional image is acquired, control passes via path 1060 to activity block 1062 wherein the previously acquired cross-sectional image is sent to one of the analysis computers.

Proceeding via path 1064 to activity block 1066, a message is received by the analysis computer which uniquely identifies the view and slice represented by the received image. The image is then analyzed by the analysis computer, while the master computer program proceeds via path 1068 to decision block 1070. In block 1070, the identity of the most recently acquired slice is checked to see if that is the last Z slice to be taken at that XY view location. If more Z slices are required, control passes via path 1072 to activity block 1074. In block 1074, the XYZ positioning table moves the circuit board in the Z direction thus positioning it for the next Z slice to be acquired. Control then proceeds via path 1076 back to activity block 1058. Another cross-sectional image is acquired in block 1058, which is sent to an analysis computer in block 1062, and identified and analyzed in block 1066. The first loop, comprising the steps 1058, 1062, 1066, 1070 and 1074, is repeated until it is determined in decision block 1070 that the last Z slice for the current XY view position has been acquired.

When the last Z slice has been acquired, control is transferred via path 1078 to activity block 1080 wherein a message indicates that the inspection of that particular XY view is complete. For example, if a particular XY view requires three different Z level slices, then the first loop will be executed three times, once for each Z level. At the completion of the third execution of the first loop, a message indicates that all data for that XY view has been acquired and analyzed.

Figure 13:
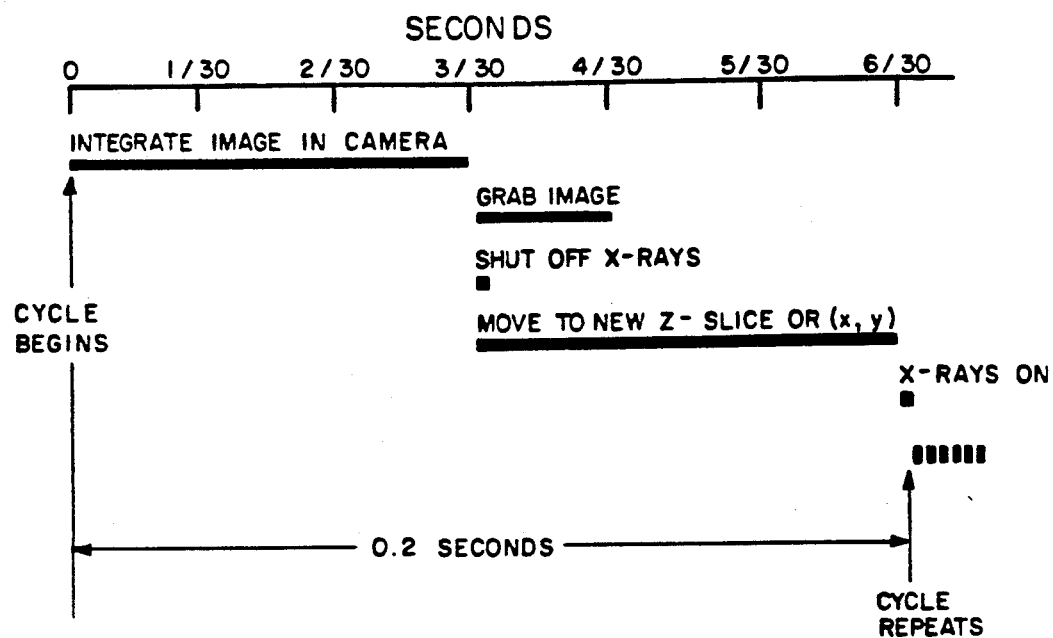
FIG. 13 is a diagram of the timing cycle for the coordinated motion of the circuit board and the acquisition of multiple field of view images.

A timing diagram for the steps identified as the first loop is shown in FIG. 13. The unit of time chosen is one frame time, or 1/30 second, which is the rate at which the images are transmitted by the camera as video signals. At the start of the first loop cycle, the circuit board is positioned at the desired inspection location, the X-rays are on, and the camera begins to integrate the image for three frame times (0.1 second). During this 0.1 second, the turntable 256 and X-ray source 280 (FIG. 3a) make one complete revolution. During the next consecutive frame time, beginning at time 3/30 seconds, the image is "grabbed" from the camera 258 and sent to one of the image analysis computers 272 (FIG. 11). Meanwhile, the master computer 272 (FIG. 11) executes a first command which stops the production of X-rays (This is accomplished by directing the electron beam 285 into the beam stop 360 in FIG. 4.) and a second command which moves the circuit board to the next view area or slice position for acquisition of another image. This movement is typically completed within 0.1 second. During this 0.1 second, the circuit board is moved to the next position and stopped. The system is preferably designed so that any mechanical vibrations caused by the movement will be substantially dampened before the end of the 0.1 second time period. The computer then executes a command which causes X-ray production to resume and the cycle is repeated. Typical cycle time for the acquisition of a single image is therefore approximately 0.2 second, corresponding to a speed of five images per second.

Even though the time required by the computer to completely analyze an image may exceed the 0.2 second image acquisition cycle time, one embodiment of the invention still performs real time image processing by utilizing the parallel processing analysis computers 272 shown in FIG. 11. The parallel processing architecture enables the system to perform several different activities simultaneously. For example, the system may simultaneously analyze several different images while also acquiring additional images. Thus, the system does not need to wait for each image analysis to be completed before subsequent images can be acquired. The optimum number of analysis computers can be determined, based upon the complexity of the image analyses being performed, such that the image processing computing does not become a bottleneck in the inspection process.

Upon completion of an XY view in block 1080, control is transferred via path 1082 to activity block 1084, wherein the results for that particular XY view inspection are stored in the memory of the master computer Proceeding via path 1086 to decision block 1088, the XY view identification is checked to determine if additional XY views of the circuit board are required.

If additional XY views are required, then control is transferred via path 1090 to activity block 1054. A second loop comprising steps 1054, 1058, 1062, 1066, 1070, 1074, 1080, 1084 and 1088 is executed multiple times until all of the programmed image locations on the circuit board have been acquired and analyzed.

When all of the programmed image locations have been inspected, control is transferred via path 1092 to activity block 1094 which indicates that the inspection is complete and it is time to unload the board.

Proceeding via path 1096 to activity block 1098, the inspection results for the previously inspected board are output in the form of an inspection report. Control then passes via path 1100 back to the beginning of the inspection routine at activity block 1050 and the system is ready to begin inspection of another circuit board.

Figure 14:
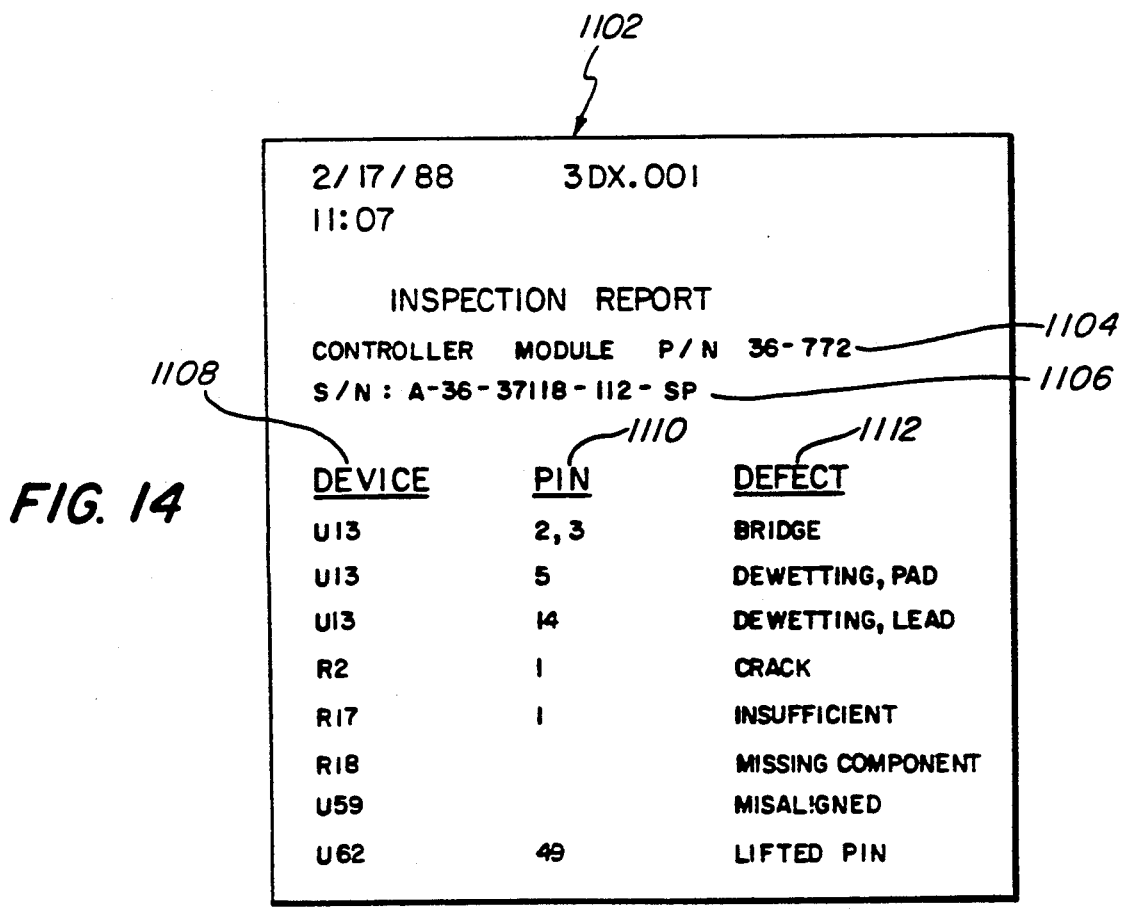
FIG. 14 is an example of an Inspection Report generated by the invention.

An example of a typical inspection report is shown in FIG. 14. Various bookkeeping entries record the date and time 1102 of the inspection, the model number of the circuit board 1104 and the serial number of the specific board inspected 1106. Results of the inspection are tabulated in three columns which identify the device name 1108, the pin number where defects were identified 1110, and the type of solder defect identified. In this particular example, it is seen that on a device identified as U13, there is a solder bridging defect between pins 2 and 3. Similarly, device R17 has insufficient solder at pin 1. The devices U13, R2, R17, etc. are typically electronic devices such as integrated circuit chips, resistors, capacitors, etc. Additionally, the inspection report may provide statistical summaries providing trend analysis of various defects and process control parameters. The inspection report may also include operation summaries showing the chronological history of the machine operation during some past period of time. The operation summaries may include a report of machine utilization factors including the identity of the operators; start times, stop times and dates for each operator's duty shift; and the number of boards processed during each shift.

The total time required to inspect an entire circuit board, utilizing the above described routine, is determined by several factors. Three of these factors are (1) the number of slices (cross-sectional images) at different Z levels needed for each XY view location, (2) the field of view size, i.e., the area covered by each individual image and (3) the size of the circuit board, i.e., the total area to be inspected.

A typical circuit board inspection may require anywhere from one to eight Z slices at each XY location, depending upon the complexity of the devices on the board and the type of solder connections. The field of view is the inspectable area acquired per image, and in one embodiment of the invention is approximately 0.400 inch by 0.375 inch. This field of view size results in high resolution images wherein each pixel has dimensions on the order of 0.0008 inch. Finally, the number of XY views and Z slices required to scan a particular circuit board, mosaic fashion, will determine the total number of views required and hence, the total amount of time required for the inspection.

For example, a 6"×9" circuit board (54 square inches), might have 50 square inches of area requiring inspection. At 0.15 square inches per field of view (0.400 inch times 0.375 inch), approximately 360 XY field of view locations are required to cover the entire board. Assuming, that an average of two Z slices are required at each location, this particular circuit board will require 720 images for a complete inspection. At the rate of five board would be approximately 144 seconds.

Typical inspection times may range from 20 seconds for very simple circuit boards up to 8 minutes for larger, more complex boards requiring high resolution inspection.

AUTOMATED SOLDER CONNECTION DEFECT ANALYSIS

The present invention is particularly will suited for performing automated inspections of the solder connections between electronic components mounted on circuit boards. In one embodiment, this is accomplished by acquiring high resolution X-ray cross-sectional images of the solder connections and analyzing the images by means of a computer controlled digital image processing procedure. There are presently a multitude of different types of solder connection defects which may be analyzed in this manner. However, the general concept of automated solder connection image analysis may be illustrated by a few illustrative examples. Such examples include bridging of solder between adjacent connection points, insufficient quantity of solder at a connection and missing solder at a connection.

Figure 15:
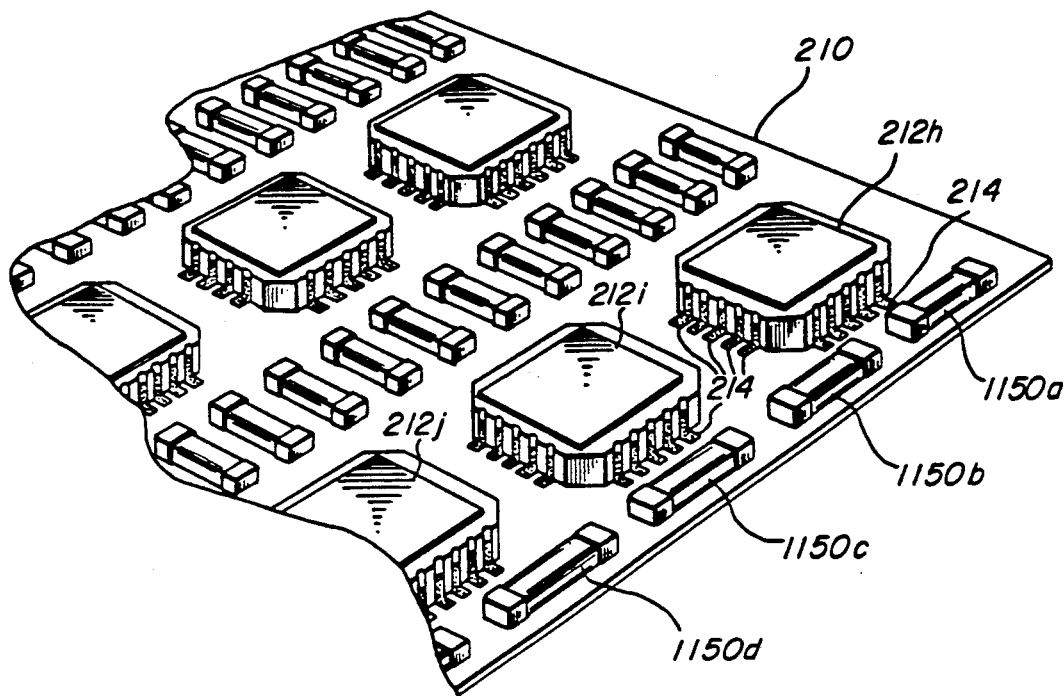
FIG. 15 shows a typical circuit upon which are located multiple electronic devices interconnected by multiple solder connections.

FIG. 15 shows a portion of a typical circuit board 210 upon which are located multiple electronic devices 212 and 1150 interconnected by multiple solder connections 214. In order to simplify the explanation of the automated analysis procedures, a specific type of electronic device and corresponding solder connection will be singled out for detailed discussion. However, it will be understood that the invention is not to be limited by the specific device chosen and that the invention applies to numerous other types of devices, technologies and electrical connections. Specifically, a device employing surface mount technology will be described in detail, however, the invention is also applicable to many other types of circuit board technologies including plated-through-hole technology.

Figure 16:
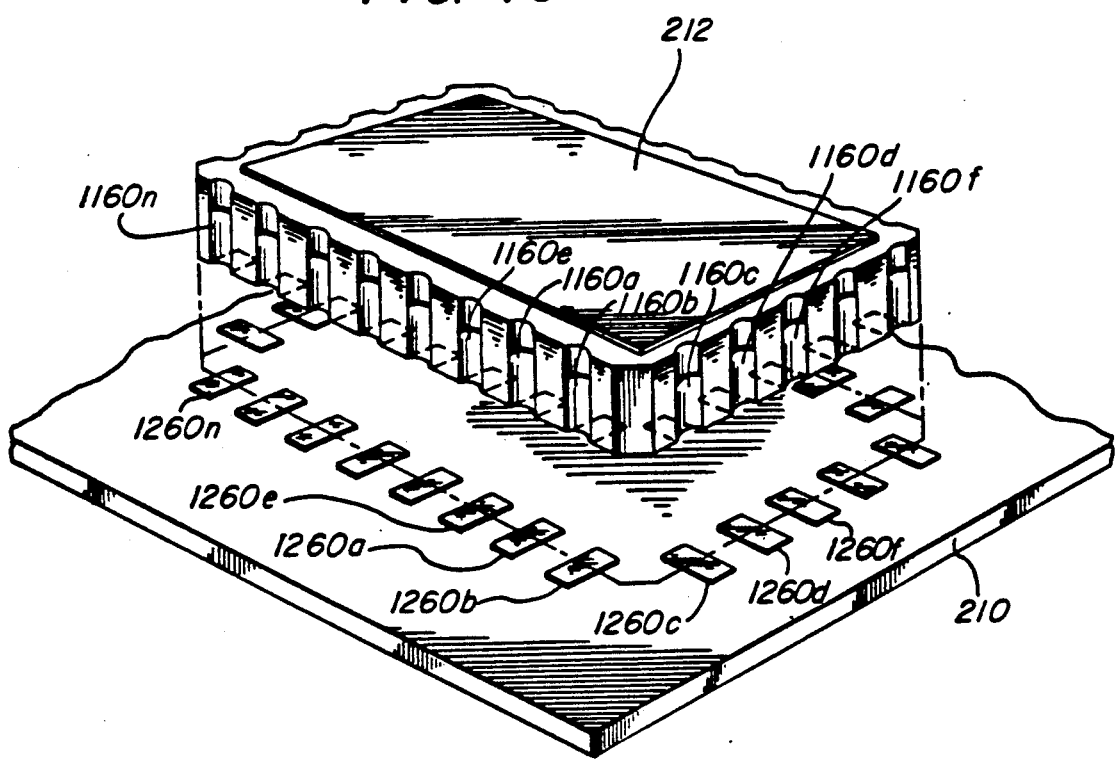
FIG. 16 shows a typical Leadless Chip Carrier device in position for mounting to a circuit board.

Surface Mount Technology (SMT) is a widely used technique wherein electronic devices comprising metallized connector pads are soldered to corresponding metallized connector pads on the surface of a circuit board. FIG. 16 illustrates a typical SMT device 212 shown in an elevated position over the mounting location on the circuit board 210 to which it will be connected. Specifically, the electronic device 212 comprises a package commonly used in the electronics industry and as known in the trade as a Leadless Chip Carrier (LCC). The LCC 212 comprises multiple metallized connector pads 1160a, 1160b, 1160c, . . . , 1160n which, when the LCC is located in position on the circuit board 210, are located immediately adjacent corresponding metallized circuit board connector pads 1260a, 1260b, 1260c, . . . , 1260n, respectively. The metallized pads 1260 are formed on or near the surface of the circuit board 210 and provide the electrical connection points for interconnecting the various electronic devices 212 and 1150 comprising the completed circuit board assembly.

Figure 17:
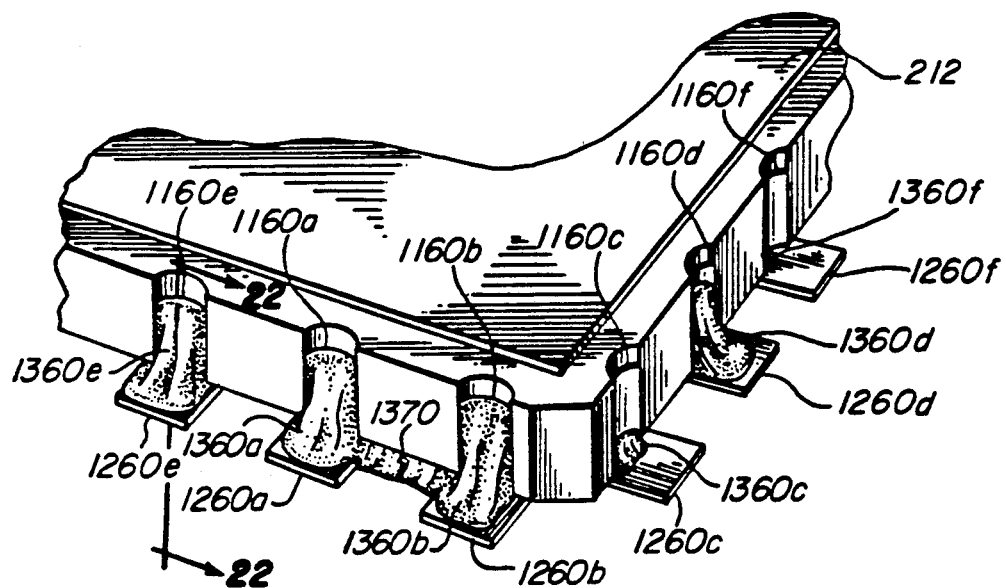
FIG. 17 shows examples of good and defective solder connections formed between an electronic device and a circuit board.

FIG. 17 is an enlarged view of a portion of the LCC 212 illustrating the general visual appearance of solder connections formed between the five metallized connector pad pairs 1160a/1260a through 1160e/1260e. Solder connection 1360e formed between pads 1160e and 1260e is an example of a good connection having no visible defects. A solder bridging defect 1370 is shown between adjacent solder connections 1360a and 1360b. A connection 1360c having insufficient solder is shown between pads 1160c and 1260c. A solder connection 1360d visually appears to have no defects but comprises internal voids. There is no solder shown at a connection 1360f between pads 1160f and 1260f.

Figure 18:
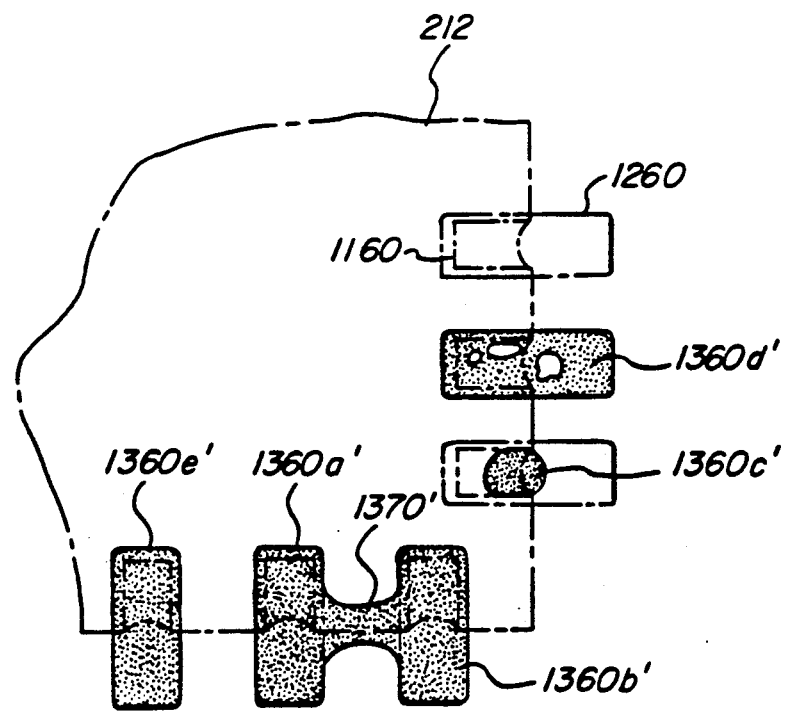
FIG. 18 shows a cross-sectional image of the solder connections in FIG. 17.

FIG. 18 illustrates the appearance of an X-ray cross-sectional image of the portion of the LCC device 212 shown in FIG. 17. The plane shown by the cross-sectional image is parallel to the plane defined by the circuit board 210 and approximately 0.0005 inch above the surface of the circuit board. The phantom lines indicating the location of the device 212, device connection pads 1160 and circuit board connection pads 1260 are shown for reference purposes only and may not be present in an actual cross-sectional image Image regions 1360a', 1360b', 1360c', 1360d', 1360e' and 1370' correspond to the solder connections 1360a, 1360b, 1360c, 1360d, 1360e and defect 1370, respectively, in the designated image plane.

IMAGE ANALYSIS FOR DETECTION OF SOLDER BRIDGING DEFECTS

Figure 19:
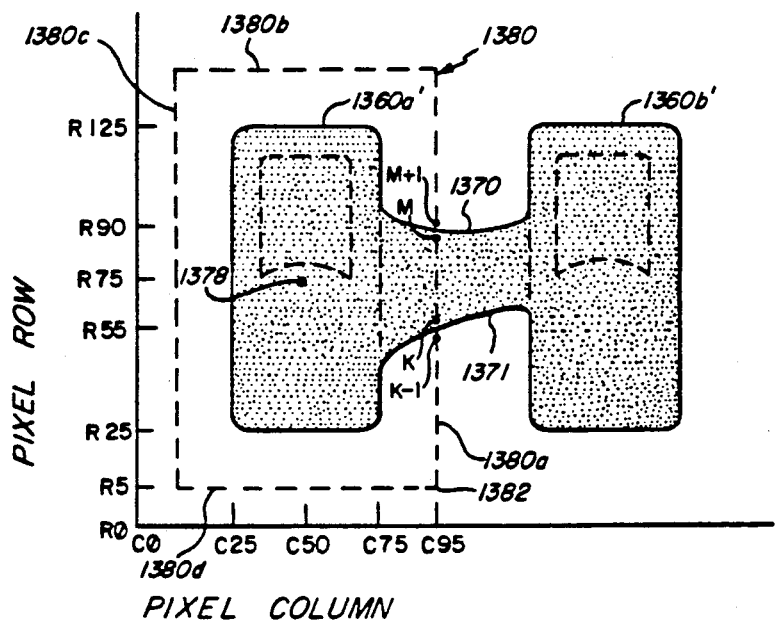
FIG. 19 illustrates the procedure for automatically locating and identifying a solder bridging type defect.

A solder bridging defect is the presence of unwanted solder between traces on a circuit board, between a connection pad and a trace, between two separate connection pads, or between two separate connection pins. An enlarged portion of FIG. 18 at the location of the bridging defect image 1370' between connection pads 1260a and 1260b is shown in FIG. 19. An arbitrary pixel grid comprising columns and rows is also shown to aid in the description of the automated procedure for detecting bridging defects.

Each pixel in the image is associated with an intensity value which corresponds to the optical density of the image represented by that pixel. The intensity values form a gray scale which ranges from zero (black) to 255 (white). The images of high density materials which readily attenuate X-rays, e.g., solder, are represented by relatively low intensity values corresponding to the darker shades of gray near the black end of the gray scale. Conversely, low density materials, e.g., plastic circuit boards, produce images having intensity values corresponding to the lighter shades of gray near the white end of the gray scale. Images having this type of gray scale are known as "positive" images. It will be understood that the relationship between shades of gray and intensity may be reversed to produce what are commonly known as "negative" images. Either negative or positive images may be used in the invention, but for purposes of explanation, positive images will be used. Therefore, pixels within the regions of the image representing solder material, e.g., regions 1360' and 1370', correspond to relatively low image intensity values. Pixels in other regions of the image represent lower density materials, e.g., plastic circuit board, and correspond to relatively high image intensity values.

The initial step in the image analysis comprises acquiring topographical data and inspection parameters necessary for performing an inspection and evaluation of a solder bridging defect. In one embodiment of the invention, a data file contains this specific information for each image analysis being performed. Once the circuit board is identified, the data file for that specific type of board is recalled and placed in the analysis computer(s) memory. An algorithm for analyzing an image for the presence of a bridging solder defect uses as input, the centroid location and boundaries of the circuit board connection pad 1260, a predetermined search path location and a predetermined differential gray value threshold. For the example shown in FIG. 19, the data file will contain the information that the centroid 1378 of connection pad 1260a is located at column and row pixel coordinates (C50,R75). Additionally, the data file will contain the information that the pixel width of pad 1260a is the difference between pixel column numbers C75 and C25 and that the pad length is the difference between pixel row numbers R125 and R25. Any other inspection parameters, such as the differential gray value threshold and search path location and dimensions, necessary for performing the bridging solder defect analysis will also be retrieved from the data file.

The procedure for analyzing the cross-sectional X-ray image of a solder connection for a solder bridging defect is illustrated in FIG. 19 with respect to solder connection 1360a, Preferably, the plane of the cross-sectional image lies in a plane which is substantially parallel to the circuit board plane and is approximately 0.0005 inch above the surface of the circuit board. The procedure generally comprises determining, from the image, the presence of unwanted solder along a search path which completely surrounds the solder connection of interest.

Using the topographical data for pad 1260a, an analysis algorithm proceeds to define a search path 1380 around the boundaries of the pad comprising path segments 1380a, 1380b, 1380c and 1380d. The search path is one pixel in width and is positioned at a predetermined distance from the boundaries of the pad. In the embodiment wherein a digital image comprises 512 columns and 480 rows and corresponds to an area on the circuit board of approximately 0.400 inch×0.375 inch, one pixel width corresponds to a distance of approximately 0.00078 inch on the circuit board. The predetermined distance between the pad boundaries and the search path in FIG. 19 is the difference between pixel columns C95 and C75 and the difference between pixel rows R5 and R25. The predetermined distance may be selected empirically to meet the requirements of any particular analysis application.

The image intensity of each pixel comprising the search path 1380 is compared to the intensity of the adjacent pixels in the search path to determine a differential gray value $\Delta G$. The image intensity or gray value of a particular pixel is given by $I_{C,R}$. The differential gray value $\Delta G_{1,2}$ between two adjacent pixels 1 and 2 is then found by taking the difference between their respective intensities $I_1$ and $I_2$. Each differential gray value $\Delta G_{1,2}$ is then compared to a predetermined threshold value $\Delta G_{Th}$. The threshold value is selected to indicate when one pixel is located in a solder portion of the image and the adjacent pixel is located in a circuit board portion of the image. The presence of unwanted solder along the search path is indicated when a differential gray value exceeds the threshold value.

By way of example, consider a search beginning at a corner 1382 of the search path 1380 located at a first pixel (C95,R5) having an intensity $I_1$ and proceeding up column C95 to the next adjacent pixel on path segment 1380a to a second pixel (C95,R6) having an intensity $I_2$. It is to be understood that this starting position is arbitrary and that any other position along the search path could also be chosen to begin the search. The differential gray value for these first two adjacent pixels is given by $$\Delta G_{1,2} = I_1 - I_2 = I_{C95,R5} - I_{C95,R6} \quad (7)$$

If the absolute value of the differential gray value $|\Delta G_{1,2}|$ is greater than or equal to the threshold value $\Delta G_{Th}$, then the location of the pixels and the sign, i.e., positive or negative, of the differential gray value are stored as candidate defect indications $D_i$, where i is an integer corresponding to the order in which the defect indication was found. For example, $D_1$ corresponds to the first defect indication encountered along the search path 1380 from the starting position 1382, $D_2$ corresponds to the second defect indication encountered and so on.

In the example shown in FIG. 19, a first defect indication $D_1$ is found at a pixel K, located approximately at (C95,R55). If pixel K is in the solder defect 1370' portion of the image, then the previous pixel K-1 in the search path, located approximately at (C95,R54), is approximately outside the solder portion and will have a higher intensity value than the pixel K. Therefore, an appropriately selected $\Delta G_{Th}$ will be smaller than the absolute value of a differential gray value $|\Delta G_{K-1,K}|$ derived from the intensities $I_{K-1}$ and $I_K$ of these two adjacent pixels K-1 and K. Additionally, $\Delta G_{K-1,K}$ is positive in sign. Similarly, a second defect indication $D_2$ is found at a pixel M located approximately at (C95,R90). If pixel M is in the solder defect 1370' portion of the image, then the subsequent pixel M+1 in the search path, located approximately at (C95,R91), is outside the solder portion and will have a higher intensity value than the pixel M. Therefore, the absolute value of a differential gray value $|\Delta G_{M,M+1}|$ derived from the intensities $I_M$ and $I_{M+1}$ of these two adjacent pixels M and M+1 is greater than $\Delta G_{Th}$. Additionally, $\Delta G_{M,M+1}$ is negative in sign. The presence of the bridge defect 1370' is thus revealed when defect indication $D_1$ is positive and the next defect indication $D_2$ is negative.

The search for defect indications continues around the path 1380 until the entire path has been examined. A report of all the bridges found is then recorded and reported.

Figure 20A:
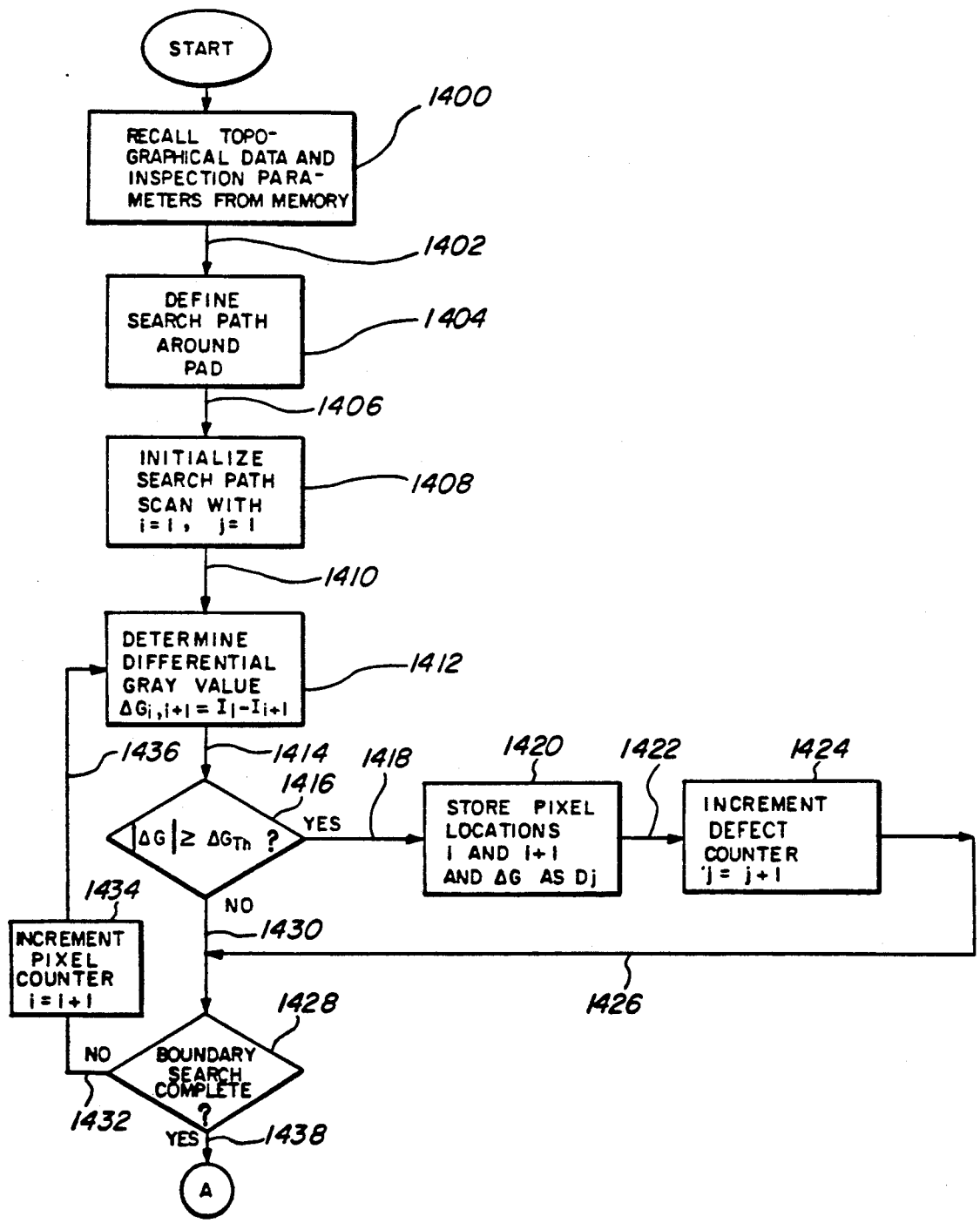
FIG. 20a is a flowchart illustrating the process for automatically locating and identifying a solder bridging defect.
Figure 20B:
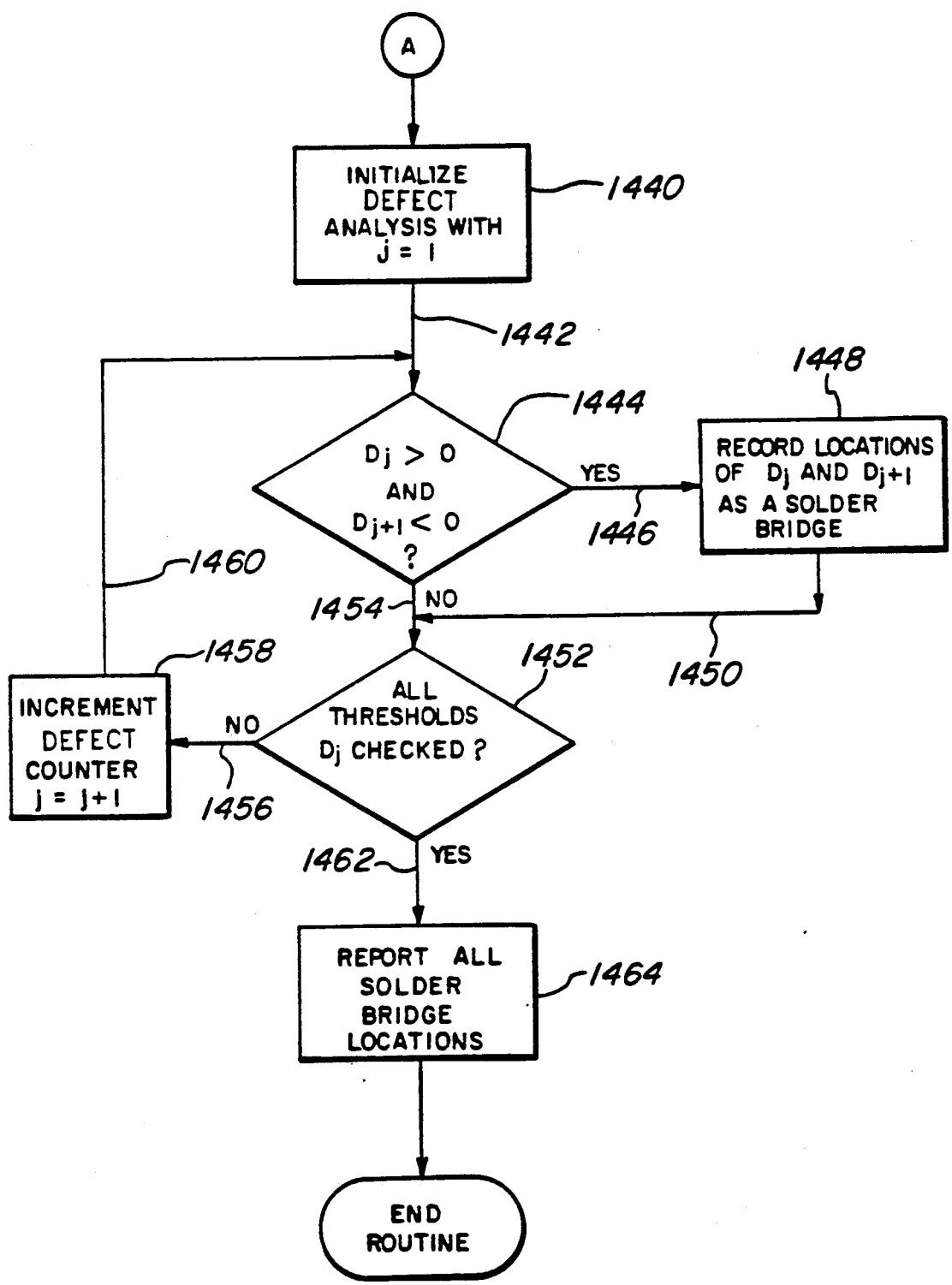

A flowchart illustrating the process for automatically locating solder bridging defects is shown in FIG. 20. Beginning in an activity block 1400, the topographical data and other inspection parameters for the particular connection pad being analyzed are recalled from the analysis computer's memory. Proceeding via a path 1402 into an activity block 1404, the search path around the connection pad is defined utilizing the topographical data and other inspection parameters stored in the memory of the computer. Control is then transferred via a path 1406 to activity block 1408 wherein the search path scan is initialized by setting a pixel counter "i" and a defect indication counter "j" equal to one.

A first loop comprising activity blocks 1412, 1416, 1420, 1424, 1428 and 1434 is entered via a path 1410 from activity block 1408. In the first loop, every pixel comprising the search path is examined, differential gray values are calculated and candidate defect locations are identified and stored for further processing at a later time. In the first activity block 1412 of the loop, the differential gray value $\Delta G_{1,2}$ for the first and second pixels in the search path is calculated. This value is passed via a path 1414 to a decision block 1416 wherein the absolute value of the differential gray value $|\Delta G_{1,2}|$ is $|\Delta G_{1,2}|$ is greater than or equal to $\Delta G_{Th}$, control passes via a path 1418 to activity block 1420. In activity block 1420, the locations of pixels 1 and 2 and the sign of $\Delta G_{1,2}$ are stored as a first defect indication $D_1$. Control passes to activity block 1424 via a path 1422 wherein the defect counter "j" is incremented by one. In a decision block 1428, the final block of the first loop, reached via a path 1426, a completion check is performed to determine if the entire search path has been examined. If not, control passes via a path 1432 to activity block 1434, wherein the search path pixel counter "i" is incremented by one. Control then returns via path 1436 to the beginning of the first loop at activity block 1412. The first loop is repeated until all of the pixels comprising the search path have been analyzed, at which time control passes out of the first loop from decision block 1428 via path 1438 to activity block 1440.

In activity block 1440, the defect counter "j" is again initialized to the value one prior to entering a second loop via path 1442. The second loop comprises blocks 1444, 1448, 1452 and 1458. In the second loop, the defect indications $D_j$, identified in the first loop, are examined to determine the locations of solder bridging defects along the search path. Entering the second loop at decision block 1444 with $j=1$, the signs of defect indications $D_1$ and $D_2$ are determined. If $D_1$ is positive and $D_2$ is negative, then control passes via path 1446 to activity block 1448 wherein the locations of $D_1$ and $D_2$ are recorded and a solder bridging defect is recorded at the search path segment between $D_1$ and $D_2$. Control then passes via path 1450 to a decision block 1452 where a completion test is performed to determine if all of the defect indications $D_j$ have been analyzed. If not, control passes via path 1456 to an activity block 1458 where the defect counter "j" is incremented by one. Control then returns via path 1460 to the beginning of the second loop at decision block 1444. The second loop is repeated until all of the defect indications $D_j$ located along the search path in the first loop have been analyzed for the solder bridging defect. Control then passes out of the second loop from decision block 1452 via path 1462 to activity block 1464. In block 1464, a report of all the solder bridging defects found along the search path is generated and stored for later recall.

IMAGE ANALYSIS FOR DETECTION OF MISSING OR INSUFFICIENT SOLDER DEFECTS

Figure 21:
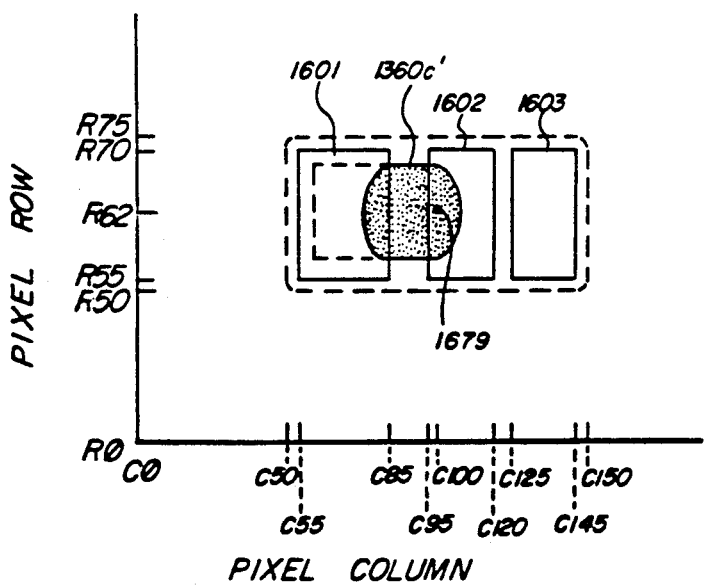
FIG. 21 illustrates the procedure for automatically locating and identifying a solder connection having insufficient solder.

A missing solder defect is defined as the presence of substantially zero or very small quantities of solder at a connection comprising an electronic device connection pad and a corresponding circuit board connection pad. An insufficient solder defect is defined as some solder present at the connection, but not enough to form a proper fillet or to provide sufficient strength to the connection. An enlarged portion of FIG. 18 at the location of the insufficient solder defect image 1360c' between connection pads 1160c and 1260c is shown in FIG. 21. An arbitrary pixel grid comprising columns and rows is also shown to aid in the description of the automated procedure for detecting missing or insufficient solder defects.

The procedure for analyzing the cross-sectional X-ray image of a solder connection for a missing solder or insufficient solder defect is illustrated in FIG. 21 with respect to solder connection image 1360c'. Preferably, the plane of the cross-sectional image lies in a plane which is substantially parallel to the circuit board plane and is approximately 0.0005 inch above the surface of the circuit board. The procedure generally comprises determining, from the image, the thickness of the solder connection in several specific regions.

Figure 22:
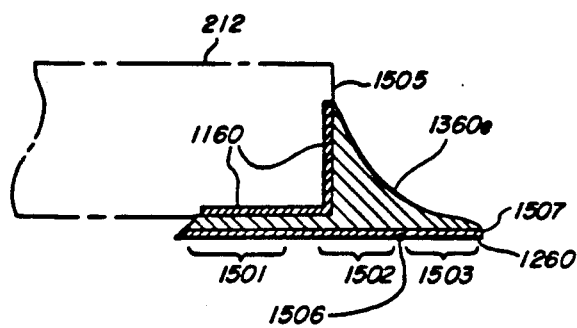
FIG. 22 is a cross-sectional view of a typical good solder connection illustrating three regions of the connection.

Three specific regions of a solder connection are defined in reference to FIG. 22. FIG. 22 is a cross-sectional view of a typical good solder connection, such as connection 1360e. The cross-sectional view is along the line 22—22 in FIG. 17. A first region 1501 of the connection 1360e, sandwiched between the device connection pad 1160 and circuit board connection pad 1260, is designated the "pad" of the connection. A second region 1502, beginning approximately at a side wall 1505 of the device 212 and extending approximately to a point 1506 between the wall 1505 and a border 1507 of the pad 1260, is designated the "heel" portion of the connection 1360e. A third region 1503, beginning approximately at the point 1506 and extending approximately to the border 1507 of the pad 1260, is designated the "toe" portion of the connection 1360e.

Typically, the pad region 1501 comprises a nearly uniform thickness of solder which is relatively thin. The heel region 1502 is generally of non-uniform thickness and comprises the thickest portion of the connection. The toe region 1503 is generally more uniform in thickness than the heel, but is not as thick. The amount of solder comprising the connection 1360e can be estimated from measurements of the average thickness of the solder in each of the three regions 1501, 1502 and 1503.

Figure 23A:
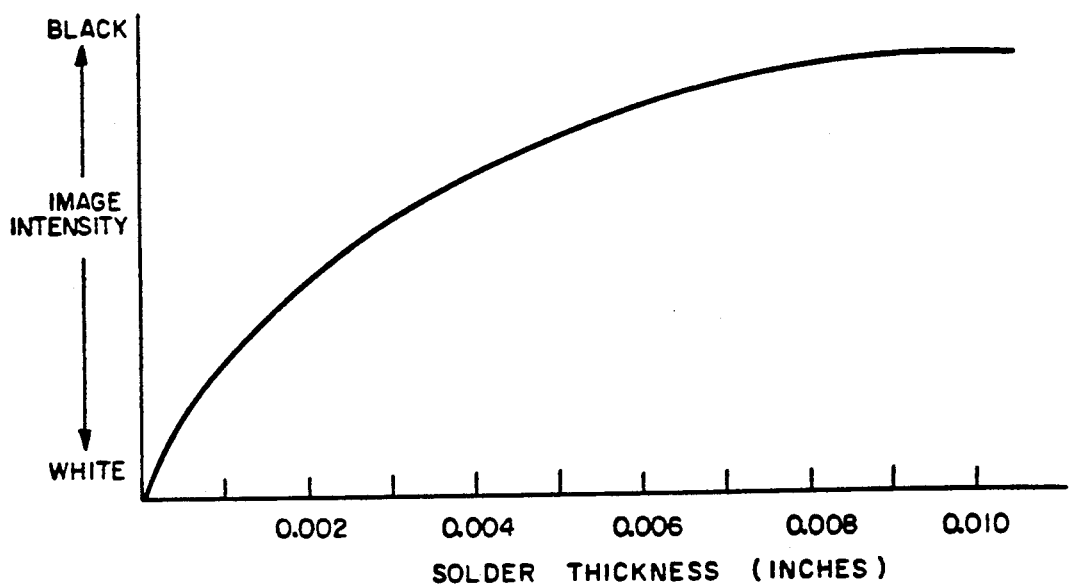
FIG. 23a is a graphical representation of the image intensity versus solder thickness for a cross-sectional image of solder material.
Figure 23B:
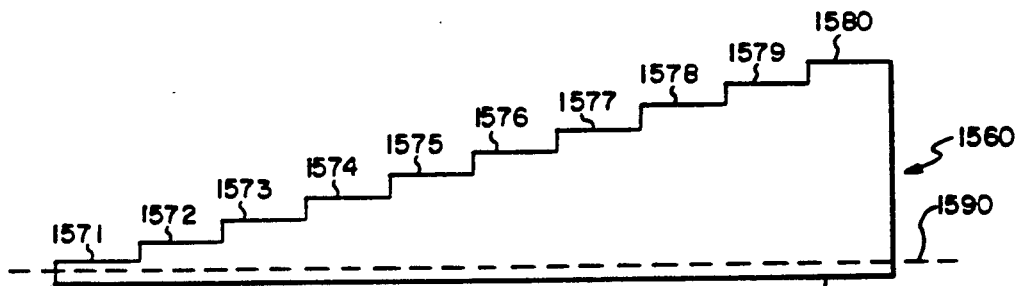
FIG. 23b shows a calibration step wedge used for calibrating the image intensity versus thickness relationship.
Figure 23C:
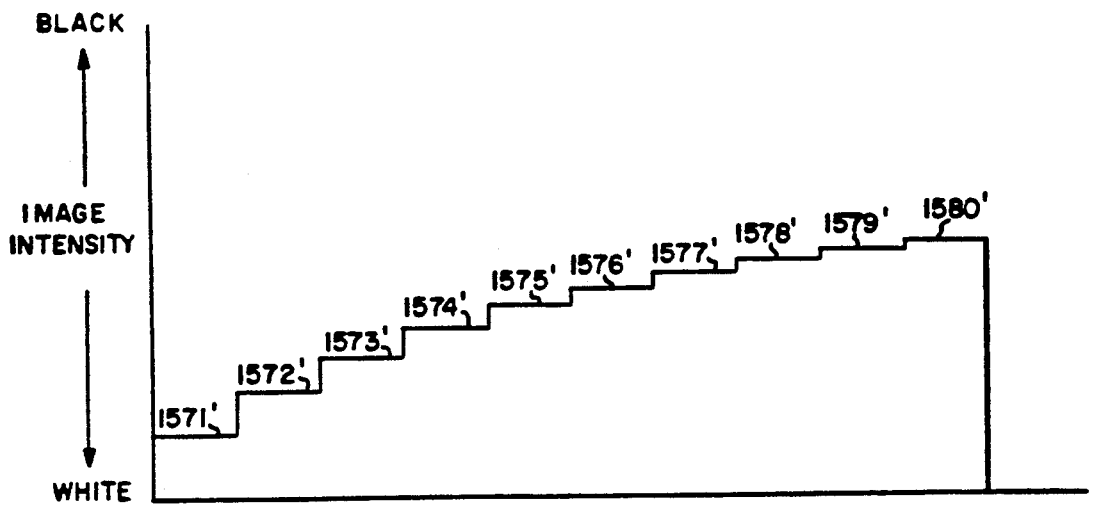
FIG. 23c is a graphical representation of the image intensity versus thickness relationship for the calibration step wedge shown in FIG. 23b.

In a laminographic cross-sectional image of solder material, typically a combination of lead and tin, there is a relationship between the intensity of the image and the thickness of the solder material forming the image. FIG. 23a illustrates an example of this general relationship. In this example, it is seen that the image intensity decreases from values corresponding to lighter shades of gray (white) to values corresponding to darker shades of gray (black) as the thickness of the solder material increases. That is, the image of a thin section of solder will have an image intensity value that is greater than the image intensity value of the image of a thicker section of solder. The image of the thin section will appear to be a lighter shade of gray than the image of the thicker section. This relationship may be calibrated by using a calibration step wedge comprising multiple steps of differing thickness. An example of such a step wedge 1560 is shown in FIG. 23b. Step wedge 1560 is constructed of solder material and comprises ten steps 1571 through 1580 having thicknesses ranging from 0.001 inch to 0.010 inch in increments of 0.001 inch. An X-ray laminographic cross-sectional image of the step wedge 1560 taken at a plane including the line 1590 and parallel to a base 1592 of the wedge exhibits the image intensity versus solder thickness relationship shown in FIG. 23c. Since the thicknesses of the steps 1571 through 1580 are known, the corresponding intensities 1571, through 1580, may be compared to intensities of other cross-sectional images of solder material where the thicknesses are not known to determine the unknown thicknesses.

The initial step in the analysis comprises acquiring topographical data and inspection parameters necessary for performing an inspection and evaluation of a missing or insufficient solder defect. One embodiment of the invention provides a data file containing this specific information for each analysis to be performed. An algorithm for analyzing an image for the presence of a missing or insufficient solder defect uses as input, the centroid location and boundaries of the connection pad, three inspection windows and six threshold values. In this example, the data file will contain the information that the centroid 1679 of connection pad 1260c is located at column and row pixel coordinates (C100,R62) in FIG. 21. Additionally, the data file will contain the information that the pixel length of pad 1260c is the difference between pixel column numbers C50 and C150 and that the pad width is the difference between pixel row numbers R75 and R50. Any other inspection parameters necessary for performing the analysis will also be retrieved from the data file.

Using the topographical data and inspection parameters for a missing or insufficient solder defect analysis of the image 1360c, at pad 1260c, the image analysis algorithm proceeds to define the boundaries of three inspection windows 1601, 1602 and 1603, shown in FIG. 21. Each window is rectangular in shape and is positioned at a predetermined distance from the boundaries and centroid of the pad. The first window 1601 is defined by four corners having pixel coordinates (C55,R55), (C55,R70), (C85,R70) and (C85,R55). Window 1601 substantially overlaps the pad region 1501 of the solder connection. The second window 1602 is defined by four corners having pixel coordinates (C95,R55), (C95,R70), (C120,R70) and (C120,R55). Window 1602 substantially overlaps the heel region 1502 of the solder connection. The third window 1603 is defined by four corners having pixel coordinates (C125,R55), (C125,R70), (C145,R70) and (C145,R55). Window 1603 substantially overlaps the toe region 1503 of the solder connection.

The average image intensity within a window is determined by summing the image intensities of all of the pixels comprising the window and dividing by the total number of pixels contributing to the sum. The average intensities thus derived from the pad region window 1601, the heel region window 1602 and the toe region window 1603 are designated $I_P$, $I_H$ and $I_T$, respectively. These average intensities, as previously discussed, are directly related to average thickness $T_P$, $T_H$, and $T_T$ of the solder in each of the respective regions. The presence of a missing or insufficient solder defect is determined by comparing these average thicknesses $T_P$, $T_H$, and $T_T$ to predetermined thickness threshold values $Th_{M,P}$, $Th_{M,H}$, $Th_{M,T}$, $Th_{I,P}$, $Th_{I,H}$, and $Th_{I,T}$. Generally, the missing solder threshold values, $Th_{M,P}$, $Th_{M,H}$ and $Th_{M,T}$, corresponding to the pad, heel and toe regions respectively, are smaller than the insufficient solder threshold values, $Th_{I,P}$, $Th_{I,H}$, and $Th_{I,T}$. That is, $Th_{M,P} < Th_{I,P}$, $Th_{M,H} < Th_{I,H}$ and $Th_{M,T} < Th_{I,T}$. Specifically, if $T_P < Th_{M,P}$, $T_H < Th_{M,H}$ and $T_T < Th_{M,T}$, then the connection is reported as having missing solder. If $Th_{M,P} < T_P < Th_{I,P}$, $Th_{M,H} < T_H < Th_{I,H}$ and $Th_{M,T} < T_T < Th_{I,T}$, then the connection is reported as having insufficient solder.

Figure 24:
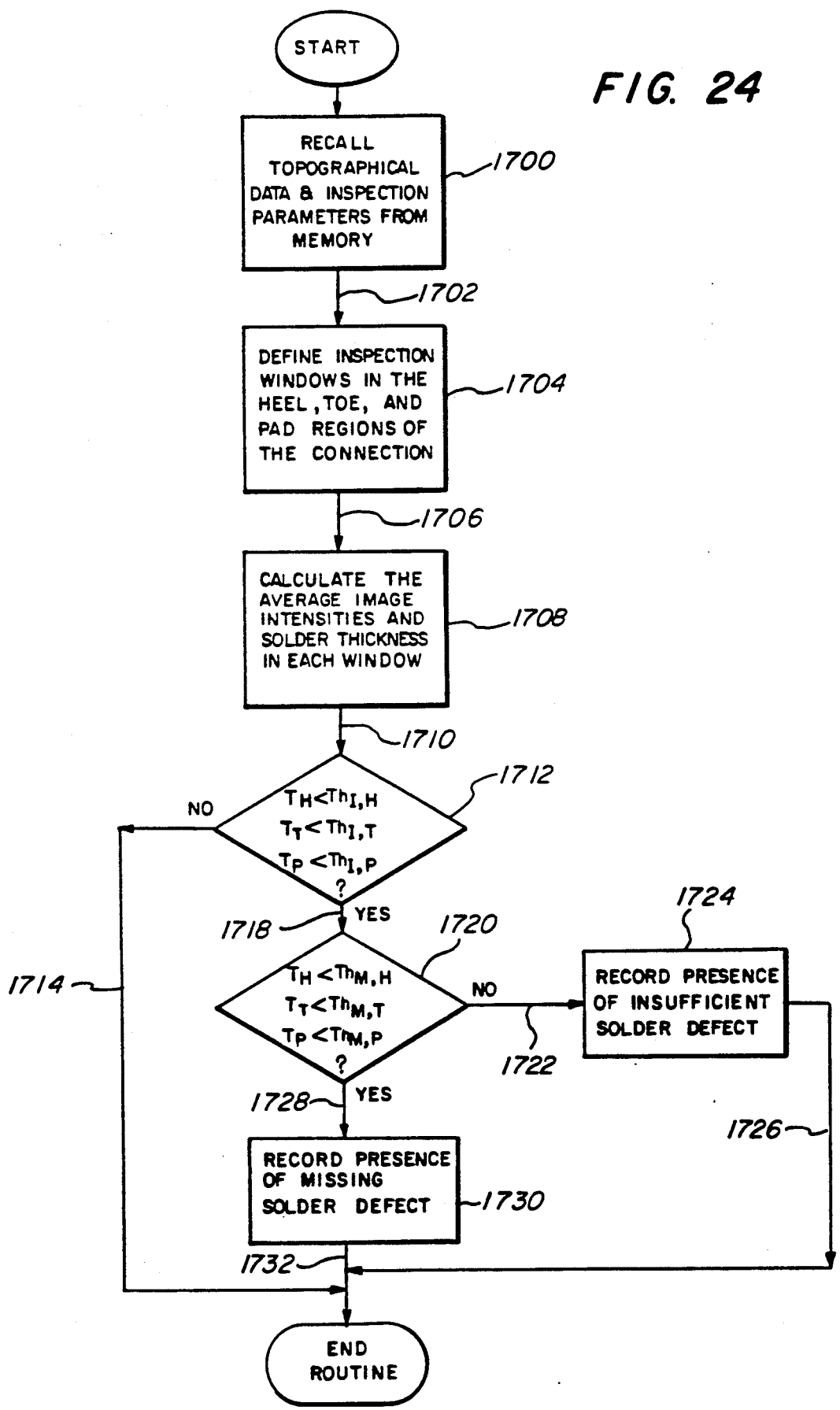
FIG. 24 is a flowchart illustrating the process for automatically locating and identifying a solder connection having missing or insufficient solder.

A flowchart illustrating the process for automatically locating missing or insufficient solder defects is shown in FIG. 24. Beginning in an activity block 1700, the topographical data and other inspection parameters for the particular connection pad being analyzed are recalled from the analysis computer's memory. Proceeding via a path 1702 into an activity block 1704, inspection windows for the pad, heel and toe regions of the solder connection are defined utilizing the topographical data and other inspection parameters stored in the memory of the computer. Control is then transferred via a path 1706 to activity block 1708 wherein the average image intensity within each window is determined and the corresponding average solder thickness is calculated. Control is then transferred to decision block 1712 via path 1710.

In decision block 1712, the average solder thicknesses $T_P$, $T_H$, and $T_T$ within the windows are compared to the insufficient solder thickness threshold values $Th_{I,P}$, $Th_{I,H}$, and $Th_{I,T}$ respectively. If the average thicknesses are not less than the insufficient solder thresholds, control passes via path 1714 to the end of the analysis routine. If the average thicknesses are less than the insufficient solder thresholds, control passes via path 1718 to decision block 1720. In decision block 1720, the average thicknesses $T_P$, $T_H$, and $T_T$ are compared to the missing solder thickness threshold values $Th_{M,P}$, $Th_{M,H}$, $Th_{M,T}$ respectively. If the average thicknesses are not less than the missing solder thresholds, control passes via path 1722 to activity block 1724 wherein the presence of an insufficient solder defect is recorded. Control then passes via path 1726 to the end of the analysis routine. If the average thicknesses are less than the missing solder thresholds in decision block 1720, control passes via path 1728 to activity block 1730 wherein the presence of a missing solder defect is recorded. Control then passes via path 1732 to the end of the routine.

The system and processes described herein were developed primarily for the inspection of solder connections on printed circuit boards. However, the invention may also be useful for the inspection of other objects and features. While the above description comprises one preferred embodiment of the invention as applied to the inspection of solder connections between electronic devices on printed circuit boards, there are other applications which will be obvious to those skilled in the art.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A solder connection inspection device comprising:
   an X-ray source comprising:
   an electron source for producing a beam of electrons;
   an anode having a surface upon which said electron beam impinges; and an electrical steering device for deflecting said electron beam to different locations on said anode surface, said steering device capable of causing said electron beam to rotate about an axis and to trace a path upon said anode surface thus causing said X-ray source to move in a first pattern, said first pattern defining a first plane;

an X-ray detector for producing an X-ray cross-sectional laminographic image of a cutting plane of said solder connection, said detector positioned to receive X-rays produced by said X-ray source which have penetrated said solder connection, said X-ray detector comprising:

a converter screen for producing an optical image corresponding to an X-ray image formed by said penetrating X-rays;

means for moving said converter screen such that it rotates about said axis and travels along a path defining a second pattern, said second pattern defining a second plane which is substantially parallel to said first plane;

an optical derotation device for transmitting said optical image from said rotating converter screen to a stationary optical image plane; and a camera located at said stationary optical image plane for detecting said optical image, said camera having an electronic output which corresponds to said optical image;

a control system for synchronizing the motions of said X-ray source and converter screen, such that said optical image representations of said X-ray cross-sectional laminographic images are formed at said stationary image plane, said control system comprising:

a sensor which monitors the position of said converter screen along said second pattern and transmits coordinates corresponding to the screen position; and a look up table which receives said coordinates from said sensor and transmits corresponding signals to said steering device thus causing said motion of said X-ray source to be synchronized with said motion of said converter screen; and a digital image processing system for analyzing said cross-sectional images and deriving from said cross-sectional images information which is indicative of features of said solder connection, said image processing system comprising:

an image digitizer for receiving said electronic image signal from said camera and forming a digital representation of said image which corresponds to said X-ray cross-sectional image of said solder connection; and a programmably-controlled computational section programmed to access predetermined regions of said digital image and to analyze said regions in accordance with a predetermined set of instructions for specific features indicative of particular types of solder defects.

2. An apparatus as defined in claim 1, wherein said X-ray source comprises a steerable electron beam X-ray tube.

3. An apparatus as defined in claim 1, wherein said electrical steering device comprises coils which produce magnetic fields which interact with said electron beam causing it to be deflected.

4. An apparatus as defined in claim 1, wherein said converter screen comprises a cadmium tungstate scintillation material.

5. An apparatus as defined in claim 1, wherein said cross-sectional image corresponds to a plane within said solder connection which is parallel to said first and second planes and intersects said axis of rotation.

6. An apparatus as defined in claim 5, wherein said image plane of said solder connection is located between said X-ray source and said X-ray detector such that the distance from said image plane to said first plane is less than the distance from said image plane to said second plane.

7. An apparatus as defined in claim 1, wherein said means for moving said converter screen further comprises a turntable which rotates about said axis and upon which said converter screen is mounted.

8. An apparatus as defined in claim 7, wherein said optical derotation device comprises first and second mirrors mounted in said turntable, said mirrors oriented at an angle of approximately 45° with respect to said axis of rotation and with respect to said first and second planes.

9. An apparatus as defined in claim 8, wherein said first mirror receives said optical image from said converter screen and reflects it to said second mirror, said second mirror further reflecting said image to said stationary image plane.

10. An apparatus as defined in claim 8, wherein said second mirror intersects said axis of rotation.

11. An apparatus as defined in claim 1, wherein said camera comprises a low light level video camera.

12. An apparatus as defined in claim 11, wherein said low light level camera comprises a silicon intensified target image intensifier.

13. An apparatus as defined in claim 1, wherein said digital image processing system comprises multiple parallel image processors.

14. A laminographic apparatus for inspecting an electrical connection comprising:

a moveable source of penetrating radiation;

a steering device for controlling the motion of said source;

an imaging system for producing a cross-sectional image of a cutting plane of said electrical connection wherein said cross-sectional image displays specific features of said electrical connection, said imaging system comprising:

a radiation detector having a variable position image forming region wherein the position of said image forming region is monitored by a position sensor which transmits coordinates corresponding to its position; and a look up table which receives said coordinates from said sensor and transmits corresponding signals to said steering device thus causing said motion of said radiation source to be synchronized with said motion of said image forming region; and an image analysis system for analyzing said image to detect said specific features, wherein said image analysis system searches said cross-sectional image for predetermined characteristics and performs predetermined analytical tests on said cross-sectional image.

15. An apparatus as defined in claim 14, wherein said imaging system comprises an X-ray source and an X-ray detector.

16. An apparatus as defined in claim 15, wherein said imaging system produces X-ray laminographs of said electrical connections.

17. An apparatus as defined in claim 16, wherein said X-ray laminographs are produced by the motion of said X-ray source and said X-ray detector with respect to said electrical connections.

18. An apparatus as defined in claim 17, wherein said motion of said X-ray source is produced by electrical means and said motion of said X-ray detector is produced by electro-mechanical means, said X-ray source and said X-ray detector motions being synchronized and controlled by an electrical feedback system.

19. An apparatus as defined in claim 17, wherein said motions of said X-ray source and said X-ray detector are substantially circular and define a source plane and a detector plane.

20. An apparatus as defined in claim 19 wherein said source plane and said detector plane are substantially parallel.

21. An apparatus as defined in claim 14, wherein one of said specific features comprises a solder bridging defect.

22. An apparatus as defined in claim 21, wherein said image analysis system calculates a series of differential image intensity gray values along a border surrounding said solder bond and compares said differential gray values to a predetermined threshold gray value.

23. An apparatus as defined in claim 22, wherein said solder bridging defect is identified by said image analysis system at locations along said border wherein said calculated differential image intensity gray values exceed said threshold value.

24. An apparatus as defined in claim 14, wherein one of said specific features comprises the quantity of solder present at said connections.

25. An apparatus as defined in claim 24, wherein said image analysis system defines three regions of said cross-sectional image corresponding to three different portions of said solder connection, calculates an average image intensity for each of said three regions and compares said average image intensities to a first and a second set of predetermined threshold values.

26. An apparatus as defined in claim 25, wherein said image analysis system identifies a missing solder defect at locations where said average intensities are less than both of said first and second sets of threshold values.

27. An apparatus as defined in claim 25, wherein said image analysis system identifies an insufficient solder defect at locations where said average intensities are less than said first set of threshold values and greater than said second set of threshold values.

28. A method of inspecting an electrical connection between electrical components mounted on a printed circuit board comprising the steps of:
producing a cross-sectional image of a cutting plane of said electrical connection which lies in a plane that is adjacent to a surface of said printed circuit board, wherein said step of producing said cross-sectional image further comprises the steps of producing X-rays with an X-ray source and detecting X-rays with an X-ray detector;
searching said cross-sectional image for predetermined features of said electrical connection; and
performing predetermined analytical tests on said cross-sectional image.

29. A method as defined in claim 28, wherein said step of producing said cross-sectional image further comprises the step of producing an X-ray laminograph of said electrical connection.

30. A method as defined in claim 29, wherein said step of producing said X-ray laminograph further comprises the steps of moving said X-ray source and said X-ray detector with respect to said electrical connection.

31. A method as defined in claim 30, wherein said step of producing said X-ray laminograph further comprises the steps of:
moving said X-ray source by electrical means;
moving said X-ray detector by electro-mechanical means; and
synchronizing said X-ray source and said X-ray detector motions with an electrical feedback system.

32. A method as defined in claim 28 wherein said step of performing predetermined analytical tests on said cross-sectional image further comprises the step of searching for specific features in said cross-sectional image.

33. A method as defined in claim 32, wherein said step of performing predetermined analytical tests further comprises the step of performing said predetermined analytical tests on said cross-sectional image at predetermined locations of said image to identify said specific features.

34. A method as defined in claim 28 wherein said step of performing predetermined analytical tests further comprise the steps of:
calculating a series of differential image intensity gray values along a border surrounding one of said electrical connections; and
comparing said differential gray value to a predetermined threshold gray value.

35. A method as defined in claim 34, further comprising the steps of identifying locations along said border wherein said calculated differential image intensity gray values exceed said threshold value and designating said locations solder bridging defects.

36. A method for identifying features of a solder joint using X-ray laminographs comprising the steps of:
producing a cross-sectional image of a cutting plane of said solder joint comprising the steps of:
providing a source of X-rays wherein X-rays are produced by an electron beam impinging upon a target;
directing said electron beam to different portions of said target, thus moving a location wherein said X-rays are produced by said X-ray source;
detecting X-rays produced by said X-ray source with an X-ray detector having a variable position image forming region;
moving the location of said X-ray detector image forming region; and
synchronizing the motion of said location of the production of said X-rays with the motion of said X-ray detector image forming region with a feedback system;
searching said cross-sectional image for predetermined characteristics; and
performing predetermined analytical tests on said cross-sectional image.

37. A method as defined in claim 36, further comprising the step of positioning a test object between said X-ray source and said X-ray detector such that said test object forms an image on said X-ray detector.

38. A method as defined in claim 37, further comprising the step of driving said feedback system in response to the motion of said detector such that said image of said test object is located at a predetermined position on said X-ray detector as said X-ray detector and said location of X-ray production move relative to said test object.

39. A method of determining the quality of an electrical connection formed between a component mounted on a circuit board and a connection pad on said circuit board comprising the steps of:
producing a high resolution cross-sectional image of a cutting plane of said electrical connection wherein said electrical connection has a first volume and said image has sufficient resolution to permit detection of a physical feature of said connection having a second volume which is substantially smaller than said first volume of said connection;
searching said cross-sectional image for said predetermined physical feature of said electrical connection;
identifying said predetermined feature found in said searching step; and
analyzing said predetermined feature to determine the effect it has on the quality of said electrical connection.

40. An apparatus for inspecting an electrical connection formed between a component mounted on a circuit board and a connection pad on said circuit board to determine the quality of the electrical connection, said apparatus comprising:
an imaging system for producing a high resolution cross-sectional image of a cutting plane of an electrical connection wherein said electrical connection has a first volume and said image has sufficient resolution to permit detection of a physical feature of said connection having a second volume which is substantially smaller than said first volume of said connection;
an image analysis system for analyzing said high resolution image to detect said physical feature, wherein said image analysis system searches said high resolution cross-sectional image for a predetermined characteristic and performs a predetermined analytical test on said cross-sectional image to determine a measure of the quality of said electrical connection.

41. An electrical connection inspection device comprising:
an X-ray source comprising:
an electron source for producing a beam of electrons;
an anode having a surface upon which said electron beam impinges; and
an electrical steering device for deflecting said electron beam to different locations on said anode surface;
an X-ray detector for producing X-ray cross-sectional laminographic images of a cutting plane of an electrical connection, wherein said detector is positioned to receive X-rays produced by said X-ray source which have penetrated said electrical connection, said X-ray detector comprising:
a converter screen having a variable position image forming region for producing an optical image corresponding to an X-ray image formed by said penetrating X-rays;
an optical transformation device for transmitting said optical image from said variable position image forming region to a stationary optical image plane; and
a camera for detecting said stationary optical image, said camera having an electronic output which corresponds to said optical image;
a control system for synchronizing the motions of said X-ray source and variable position image forming region such that said optical image representations of said X-ray cross-sectional laminographic images are formed at said stationary image plane, said control system comprising:
a sensor which monitors the position of said variable position image forming region and transmits coordinates corresponding to said image forming region position; and
a look up table which receives said coordinates from said sensor and transmits corresponding signals to said steering device thus causing said motion of said X-ray source to be synchronized with said motion of said variable position image forming region; and
a digital image processing system for analyzing said cross-sectional images of said electrical connection, said image processing system comprising:
an image digitizer for receiving said electronic image signal from said camera and forming a digital representation of said image which corresponds to said X-ray cross-sectional image of said electrical connection; and
a programmably-controlled computational section programed to access predetermined regions of said digital image and to analyze said regions in accordance with a predetermined set of instructions for specific features of said electrical connection.

42. A method for determining the quality of an electrical connection comprising the steps of:
producing a cross-sectional image of a cutting plane of said electrical connection;
searching said cross-sectional image for a specific feature in accordance with a predetermined set of instructions; and
analyzing said specific features in order to determine the quality of said electrical connection.

43. An apparatus for measuring a physical characteristic of an electrical connection comprising:
a radiation source for providing a beam of transmissive radiation;
an imager which detects transmissive radiation which is transmitted through said electrical connection and generates a cross-sectional electronic image of a cutting plane of said electrical connection;
an image converter for converting said electronic image into a gray scale coded image; and
an image processor comprising a library of analysis algorithms and predetermined inspection parameters wherein said processor receives said gray scale coded image, analyzes said gray scale coded image utilizing said analysis algorithms from said library thus performing predetermined computational analysis on said gray scale coded image based upon each selected analysis algorithm, and provides an output corresponding to a physical characteristic of said electrical connection.

44. A method of detecting and characterizing a structural feature of an electrical connection, comprising the steps of:
exposing an electrical connection to a beam of transmissive radiation having sufficient energy to penetrate said electrical connection;

detecting transmissive radiation which is transmitted through said electrical connection to create an electronic cross-sectional image of a cutting plane of said electrical connection;

converting said electronic cross-sectional image into a gray scale coded image;
providing an analysis algorithm; and
performing a predetermined computational analysis on said gray scale coded image using said analysis algorithm.

* * * * *